US009382576B2

(12) United States Patent
Yang et al.

(10) Patent No.: US 9,382,576 B2
(45) Date of Patent: Jul. 5, 2016

(54) METHOD FOR ISOLATING AND PURIFYING RNA FROM BIOLOGICAL MATERIALS

(75) Inventors: Xianglong Yang, Tianjin (CN); Xuejing Li, Tianjin (CN)

(73) Assignee: TIANJIN SPRINGTIDE BIOTECH CO., LTD., Tianjin (CN)

( * ) Notice: Subject to any disclaimer, the term of this patent is extended or adjusted under 35 U.S.C. 154(b) by 281 days.

(21) Appl. No.: 14/117,035

(22) PCT Filed: Feb. 24, 2012

(86) PCT No.: PCT/CN2012/071598
§ 371 (c)(1),
(2), (4) Date: Dec. 22, 2014

(87) PCT Pub. No.: WO2012/155577
PCT Pub. Date: Nov. 22, 2012

(65) Prior Publication Data
US 2015/0112054 A1    Apr. 23, 2015

(30) Foreign Application Priority Data

May 18, 2011 (CN) .......................... 2011 1 0129253

(51) Int. Cl.
*C07H 21/00* (2006.01)
*C12Q 1/68* (2006.01)
*C12N 15/10* (2006.01)
*C07H 1/06* (2006.01)
*C07H 1/08* (2006.01)

(52) U.S. Cl.
CPC .......... *C12Q 1/6806* (2013.01); *C12N 15/1003* (2013.01); *C07H 1/06* (2013.01); *C07H 1/08* (2013.01)

(58) Field of Classification Search
None
See application file for complete search history.

(56) References Cited

U.S. PATENT DOCUMENTS 5,728,822 A * 3/1998 MacFarlane .......... C07C 211/62
536/25.41

OTHER PUBLICATIONS

Hooft et al. The EMBO Journal (1985), vol. 4, pp. 2167-2171.*

* cited by examiner

*Primary Examiner* — Patrick Lewis
(74) *Attorney, Agent, or Firm* — George G. Wang; Bei & Ocean

(57) ABSTRACT

Includes the following steps: (1) Mix organs and tissues with formamide and monovalent cation salt solution, homogenize them to obtain the dehydrated biological sample; (2) Mix the dehydrated biological sample with monovalent cation salt solution for incubation; (3) Add the monovalent cation salt solution with precipitation effect to the mixture, mix them and centrifuge, then pour the supernatant into another centrifuge tube; (4) Add isopropanol, mix it and centrifuge, and then discard the upper phase liquid, the lower phase liquid and the visible residual impurities between the upper and lower phases to get white RNA precipitate. This method proposed in the invention enables efficient isolation of protein from RNA in the biological samples. It avoids decomposition of RNA by the residual protein that remains in the products; the reagent used in the invention is low-toxicity compound with little hazard to the environment and human body; since the products obtained are not easily decomposed, the products can be transported at long distance and stored at room temperature; the method is easy to operate and no special skill is required for the operator. The equipment used is simple and cost efficient and enables high RNA yield and high purity.

8 Claims, 18 Drawing Sheets

1.2% agarose gel electrophoresis

METHOD FOR ISOLATING AND PURIFYING RNA FROM BIOLOGICAL MATERIALS

CROSS-REFERENCE TO RELATED APPLICATIONS

This application claims priority from CN Application No. CN201110129253.5, filed May 18, 2011 and PCT Application No. PCT/CN2012/071598, filed Feb. 24, 2012, the contents of which are incorporated herein in the entirety by reference.

FIELD OF THE INVENTION

The invention relates to a RNA purification and isolation method.

BACKGROUND OF THE INVENTION

Nucleic acids, including deoxyribonucleic acid (DNA) and ribonucleic acid (RNA), are present in all cells. DNA is the genetic substance of the cell, on which the genes can be transcribed into messenger RNA (mRNA), and the corresponding genetic information carried by the latter will be translated into a protein with functional activity. In addition to mRNA, there are other RNAs, including transfer RNA (tRNA), ribosomal RNA (rRNA), interference RNA (iRNA), micro RNA (miRNA), and heterologous nuclear RNA (hnRNA). Analyzing gene expression and regulation through assessment of mRNA, iRNA and miRNA in tissues or cells is an extremely important method in the field of life science, and provides a very large number of physiological indicators for cells. A wide range of techniques can be used to assess mRNA, iRNA and miRNA level, including polymerase chain reaction (PCR), quantitative polymerase chain reaction (qPCR), real-time PCR (Real-Time PCR), Northern blotting, bio-chip, and transcriptome sequencing, etc. When using each of these techniques, it is necessary to use the isolated RNA samples, and the RNA samples should not contain the following contaminant found in active cells: genomic DNA, protein, fat, polyphenols, polysaccharides and certain other biological molecules. [Wyatt, J. R, and Tinoco, I. J. (1993) RNA structure and RNA function, in The RNA World (Gesteland, R. F and Atkins, J. F., eds.), Cold Spring Harbore Laboratory Press, Cold Spring Harbor, N.Y., pp. 465-496.]

To separate RNA from a kind of biological material, RNA must be separated from DNA and other ingredients constituting the biological specimens. The key of RNA purification is: 1. All enzymes that have nuclease activity, including nucleic acid enzymes (RNases), must be deactivated to prevent decomposition of RNA by these enzymes. Peel off the attached protein on the natural RNA to release the bare RNA to the solution; this can prevent the RNA from being removed together with the attached protein as impurities, resulting in increased RNA extraction yield. At the same time, it also helps prevent RNA decomposition caused by residual trace protein in the obtained RNA samples, which improves the quality and purity of the isolated RNA. The obtained RNA samples must not contain any protein residue, because these protein residues usually contain enzymes with RNases activity, which will lead to RNA decomposition.

In addition to nuclease, many other enzymes in the cell also have RNase activity, such as the variety of DNA polymerases, transcription enzymes, reverse transcriptase enzymes with RNase activity that are present in eukaryotic and prokaryotic cells. Therefore, the key to preventing RNA decomposition is completely inhibiting the activity of all enzymes, including RNases, prior to RNA extraction. Thus, in the RNA samples obtained, even trace protein must be removed since it may contain some enzymes with RNase activity, which may cause the RNA obtained to be quickly decomposed.

Many scientists invented and expounded a variety of RNA isolation method. Most of these methods depend on cesium chloride density gradient centrifugation or phenol chloroform extraction. However, the isolation process is time-consuming, and uses hazardous reagents that pose threat to the environment and human body. In addition, the samples are easily contaminated by exogenous nucleic acid and protein. [U.S. Pat. Nos. 5,075,430; 5,234,809; 5,155,018; 6,277,648; 6,875,857; 6,958,392; 6,953,686; 6,310,199; 6,992,182; 6,475,388; 5,075,430; 7,074,916; U.S. Patent Publication No. 20060024701; European Patent No. EP0765335; Boom et al. 1990, J. Clinical Microbiology 28: 495; Cox, R. A. (1968) The use of guanidinium chloride in the isolation of nucleic acids Methods Enzymol 12, Part B, 120-129; Chirgwin, J, M., Przybyka, A. E., Mac Donald, R. J., Rutter, W. J. (1979) Isolation of biologically active ribonucleic acid from sources enriched in ribonuclease. Biochemistry 18(24), 5294-5299]

In early RNA extraction experiments, usually phenol and chloroform were used for protein extraction [Kirby, K S (1968) Isolation of Nucleic Acids with Phenolic Solutions, Methods Enzymol 12, part B, 87-99.]; With this method, a large amount of RNA molecule for which the protein is not completely peeled off will be removed as impurities together with the proteins removed; furthermore, some RNA in the obtained RNA samples still contain a small amount of protein, so repeated phenol and chloroform extraction is required to remove the residual protein. This results in a very low yield of extracted RNA, and the entire RNA extraction process is complicated and lengthy, and the trace protein that's not completely removed often causes the extracted RNA to be decomposed. [Ingle, J. and Burns, R. G. (1968) The loss of ribosomal ribonucleic acid during the preparation of nucleic acid from certain plant tissues by the detergent-pjenol method, Biochem J. 110, 605, 606]

In order to address the various defects of the phenol and chloroform extraction method used to extract RNA, cesium chloride gradient centrifugation method was used to selectively precipitate RNA to obtain high-purity nucleic acid, which provides a good alternative to phenol and chloroform extraction. However, this method requires very expensive equipment, strict operational training and complicated operation, which inhibits its application in general-purpose laboratories and cannot be widely adopted. [Glisin, V., Crkvenjakov, R., and Byus, C (1974) Ribonucleic and isolated by cesium chloride centrifugation. Biochemistry 13, 2633-2637.]

Currently the most widely used method is the technique invented by P. Chomczynski (U.S. Pat. No. 5,945,515), which he expounded in his published thesis. [Chomczynski, P. and Sacchi, N, (1987) Single-step method of RNA isolation of biologically active ribonucleic acid from sources enriched in ribonuclease. Biocemistry 18, 5294-5299; and Sacchi, N, (1987) Single-step method of RNA isolation by acid guanidinium thiocyanate-phenol-chloroform extraction Anal Bilchem 162(1), 156-159.]

In his patent, P. Chomczynski discloses a solution that enables simultaneous isolation of RNA, DNA and protein. The solution contains guanidine thiocyanate, 40 to 60% of phenol, glycerin used as phenol stabilizer, and the buffer used to maintain a solution pH of 4. The solution is a homogeneous mixture (i.e., single-phase liquid), and addition of 10% chloroform may lead to effective phase-split and enable RNA to be assigned to the aqueous phase, and the protein and DNA are concentrated in between the organic phase and two phases. Adding an equal volume of isopropanol to the aqueous phase results in RNA precipitation. The RNA precipitate obtained through centrifugation can be washed using 70% ethanol and dried.

Compared with the traditional technique, the advantage of this method is the time needed is less than 1 hour and the operation intensity is also greatly reduced. It provides high product purity and high efficiency. However, due to the following problems, it can only be used in the laboratory, and cannot be widely adopted:

It requires expensive laboratory facilities and supplies, such as high-speed refrigerated centrifuge, liquid nitrogen, low-temperature refrigerator, a fume hood.

It requires skilled technical staff. To use this method, you need trained and highly specialized personnel with rich experience in experimental work.

The supplies used, such as centrifuge tubes, micro pipette tip, glassware and reagents, require DEPC water treatment or high-temperature, long-time baking to prevent RNA decomposition by the intractable RNases. This requires a lot of time and effort.

The method not only uses highly toxic phenol and chloroform, but uses high-concentration (2~5M) guanidine salt solution with acute toxicity, which are extremely harmful to human health—guanidine thiocyanate and guanidine hydrochloride are defined as hazardous materials by CHIP (Commonwealth Chemicals Hazard Information and Packaging) and are defined as toxic reagents by HCS (United States Hazard Communication Standard).

E. Although the combined effect of high-concentration guanidinium salts, phenol and chloroform in peeling protein off from RNA is greatly improved, the protein cannot be completely removed, which often leads to decreased yield of RNA extracted from some biological materials, and since a small amount of residual protein is present in the RNA sample obtained, the Rnases contained in the residual protein can cause RNA decomposition.

F. Furthermore, for tissues that do not dissolve in guanidine salt, particularly most tissues in plants, the isolation method using high-concentration guanidine salt does not produce any RNA.

SUMMARY OF THE INVENTIONS

The aim of the invention is to address the defects in existing technologies and provide a safe, simple, fast and efficient method for isolating and purifying RNA from biological materials which both applies to general laboratory experiments and industrial production.

The technical solution of the invention is summarized as follows:

The method for isolating and purifying RNA from biological materials includes the following steps:

(1) Use One of the Following Methods to Prepare Dehydrated Biological Sample:

Method I: Add tissues and organs to the mixture of formamide with a volume ratio of 1000:0-1000 and 3M-13.5M monovalent cation salt solution, and homogenize for 5 s~20 min at 0~25° C. to obtain a dehydrated biological sample; the ratio between the said tissues and organs and the mixture is 0.5~200 mg:1 ml. The said tissues and organs are tissues and organs of animals, plants, or fungi;

Method II: Add the single-cell precipitate to the mixture of formamide with a volume ratio of 1000:0-1000 and 3M-13.5M monovalent cation salt solution, suspend it at 0~25° C. or homogenize at 0~37° C. for 20 s~20 min to obtain a dehydrated biological sample; the said single cell precipitate is obtained from Gram positive bacteria cultured cells, Gram negative bacteria cultured cells, fungi cultured cells, cultured cells of animals, cultured cells of plants, blood cells or sperm cells;

(2) Mix the dehydrated biological sample with 3M-13.5M monovalent cation salt solution at a volume ratio of 200: 0~200, or mix the dehydrated biological sample with 3M-13.5M monovalent cation salt solution and Formamide solution containing sodium dodecyl sulfate with mass concentration of 5%-40% at a volume ratio of 160:50:40, incubate at 0~95° C. for 0.5~120 min, and leave it at 0~40° C. for 0~10 min;

(3) Add 3.3M-5M monovalent cation salt solution with precipitation effect to the mixture obtained in step (2) at a volume ratio of 200:400~1000, mix it, centrifuge for 0.15~30 min at 2000~16000 g at 4~25° C., and then pour the supernatant into another centrifuge tube;

(4) Add isopropanol to the supernatant at a volume ratio of 900:300~800, mix it, centrifuge for 1~30 min at 2000~16000 g at 4~37° C., and then discard the upper phase liquid, the lower phase liquid and the visible residual solid impurity between the upper and lower phases to get white RNA precipitate at the bottom of the centrifuge tube.

The said process also includes the following steps: Wash the white RNA precipitate using aqueous ethanol solution with volume percentage concentration of 70%-80%; centrifuge for 10~60 s at 2000~16000 g at 4~37° C. discard the washing liquid and dry the precipitate.

The ratio between the said tissues and organs and the said mixture is 5~100 mg: 1 ml.

The said monovalent cation salt is lithium chloride, sodium chloride or potassium chloride (at least one of the three).

The said monovalent cation salt is sodium chloride or lithium chloride.

The said monovalent cation salt used for precipitation is lithium chloride, sodium chloride or potassium chloride (at least one of the three).

The said monovalent cation salt used for precipitation is sodium chloride and potassium chloride.

The said step (4) is as follows: Add isopropanol to the supernatant at a volume ratio of 700:400~600, mix it, centrifuge for 2 min at 8000~12000 g at 20~25° C., and then discard the upper phase liquid, the lower phase liquid and the visible residual solid impurity between the upper and lower phases to get white RNA precipitate at the bottom of the centrifuge tube.

The experiment shows that the method proposed in the invention can efficiently peel off the protein on RNA in the biological samples to obtain pure RNA. It avoids decomposition of RNA by the residual protein that remains in the product generated using existing techniques; the reagent used in the invention is low-toxicity compound with little hazard to the environment and human body; since the products obtained are not easily decomposed, the products can be transported at long distances and stored at room temperature; the method is easy to operate and no special skill is required for the operator. The equipment used is simple and cost efficient and enables high RNA yield and high purity.

The invention is designed for both general laboratory applications and industrial production.

DETAILED DESCRIPTION OF PARTICULAR EMBODIMENTS OF THE INVENTION

Figure 1:
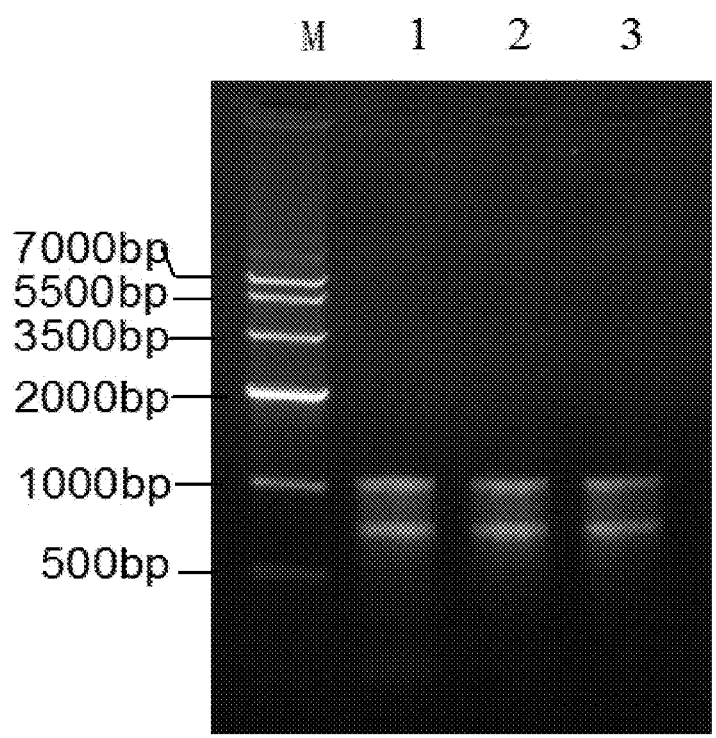
FIG. 1 is the product electropherogram obtained in Example 1 and Example 2.

The following examples can help technical professionals in this field understand this invention. It will not set any limit to the invention.

Example 1

RNA in the *E. coli* Cells Suspended in Formamide does not Decompose at High Temperature The method for isolating and purifying RNA from biological materials includes the following steps:
(1) Conduct overnight cultivation of the LB medium inoculated with *E. coli* strain JM109 (purchased from Beijing DingGuo ChangSheng Biotechnology Co., Ltd.) in the shaker at 37° C. with 180 rev/min; add 1 ml of the *E. coli* culture broth in a 1.5 ml centrifuge tube, after centrifugation at 8000 g for 1 min at room temperature, discard the liquid; repeat the above process of centrifugation and then absorb the residual liquid by using a micro pipette to obtain the *E. coli* strain JM109 cells precipitate; add 160 µl formamide to the *E. coli* strain JM109 cells precipitate and suspend at 250° C. for 15 s to obtain the dehydrated biological sample; ratio of the *E. coli* strain JM109 cells precipitate and formamide is 5 mg: 160 µl;
(2) Add 40 µl formamide solution of sodium dodecyl sulfate (SDS) with the mass percentage concentration of 20% to 160 µl dehydrated biological sample, mix and incubate at 80° C. for 10 min to rupture the bacterial cells and then leave it at 0° C. for 5 min;
(3) Add 600 µl 3.3M NaCl aqueous solution which has precipitation effect to the product obtained in step (2), after vortex oscillation blending, conduct ice bath for 5 min and centrifugation at 8000 g for 1 min at 4° C., pour this supernatant into another centrifuge tube;
(4) Add 600 µl isopropanol to the supernatant, mix them; after centrifugation at 8000 g for 2 min at 4° C., discard the liquid; thus the white RNA precipitate can be obtained at the bottom of the centrifuge tube.

Wash the precipitate at the bottom of the centrifuge tube by using aqueous ethanol solution with volume percentage concentration of 70%; after centrifugation at 8000 g at 4° C. for 30 seconds, discard the washing liquid, then put the centrifuge tube on the filter paper to dry the precipitate. Add 150 µl water for injection to dissolve the precipitate, which will be used for detection.

Agarose gel electrophoresis test: Take 0.4 µl of the above RNA aqueous sample to conduct 4V/cm voltage electrophoresis in 1.2% of non-denaturing agarose the gel (1×TAE electrophoresis buffer) for 30 min.

Results of agarose gel electrophoresis: As shown in the first band of FIG. 1 (the electrophoresis patterns), the 16s rRNA and 23s rRNA of the *E. coli* RNA solution samples are neatly edged, which proves that the RNA molecule extracted from the *E. coli* RNA solution is not decomposed.

Summary: The results of Example 1 illustrate that after formamide suspension of *E. coli* cells, all enzymes of RNases activity in the formamide solution can be completely inhibited in the process of incubation of the cells at 80° C. and decomposition of RNA molecule can be prevented.

Example 2

Nuclease in RNA Samples can be Removed Using the Method of Extracting Impurities with Isopropanol and Precipitating RNA by Centrifugation The method for isolating and purifying RNA from biological materials includes the following steps:
Steps (1)-(2) are the same as described in Example 1;
(3) Add 700 µl 3.57M NaCl, 1.14 M KCl aqueous solution which has precipitation effect to the 200 µl product obtained in step (2); after vortex oscillation blending and centrifugation at 16000 g for 5 min at room temperature, pour this supernatant into another centrifuge tube;
(4) Add 500 µl isopropanol to the supernatant, mix them, after centrifugation at 16000 g for 10 min at 25° C., discard the upper phase liquid, the lower phase liquid and visible residual solid impurities between the upper and lower phase, thus the white RNA precipitate can be obtained at the bottom of the centrifuge tube.

Wash the white RNA precipitate using aqueous ethanol solution with volume percentage concentration of 80%; after centrifugation at 16000 g at room temperature for 10 s, discard the washing liquid and dry the precipitate.

Add 150 µl water for injection (without RNases contamination) to dissolve the precipitate, then add 50 µl RNA sample into the two centrifuge tubes respectively; incubate them for 5 min and 60 min respectively at 70° C.; then cool down the two centrifuge tubes at room temperature.

Agarose gel electrophoresis test: Same as the agarose gel electrophoresis method described in Example 1.

Results of agarose gel electrophoresis: As like the electrophoresis patterns shown in FIG. 1, NO.2, No.3 RNA samples were insulated for 5 min and 60 min respectively at 70° C. The results show that the samples are the same after the two kinds of incubation of the *E. coli* RNA solution. That is, both of their 16s rRNA and 23s rRNA are neatly edged, which proves that the RNA molecules extracted from the *E. coli* RNA solution are not decomposed after the long-time insulation.

Summary of Example 2: *E. coli* cell RNA can be obtained using the method of extracting impurities with isopropanol and precipitating RNA by centrifugation. The obtained RNA solution sample does not contain any nuclease that can decompose RNA.

Example 3

SDS in Formamide Facilitates the Separation of Protein-RNA Complexes

The method for isolating and purifying RNA from biological materials includes the following steps:

Weigh a certain mass of SDS solids respectively and put them in a 1.5 ml centrifuge tube. Then add 1 ml formamide solution and insulate for 10 min at 70° C. to dissolve the SDS solids and thus formamide solution of 1%, 2%, 3%, 4%, 5%, 6%, 7% SDS can be obtained; conduct overnight cultivation of the LB medium inoculated with *E. coli* strain JM109 in the shaker at 37° C. with 180 rev/min; add 2 ml of the overnight cultivated broth to 100 ml LB medium which was insulated at 37° C. and then cultivate for 3 to 4 hours in the shaker at 37° C. with 180 rev/min and its 600 nm absorbance value will reach about 0.8; add 1 ml *E. coli* culture broth to ten 1.5 ml centrifuge tubes respectively, after centrifugation at more than 8000 g for 1 min, discard the liquid; repeat the above process of centrifugation and absorb the residual liquid. Using formamide which contains 0.00% (control group), 1%, 2%, 3%, 4%, 5%, 6%, 7% SDS respectively to suspend the cell precipitate in the centrifuge tubes.

Incubate the centrifuge tubes for 10 min at 80° C. to rupture the bacterial cells. Then conduct ice bath for the centrifuge tubes for more than 5 min;

Steps (3)~(4) are the same as described in Example 2;

Wash the white RNA precipitate using aqueous ethanol solution with volume percentage concentration of 80%; after centrifugation at 16000 g at room temperature for 10 s, discard the washing liquid and dry the precipitate. Add 150 µl water for injection (without RNases contamination) to dissolve the precipitate.

Agarose gel electrophoresis: Same as the agarose gel electrophoresis method described in Example 1.

Figures 1, 2:
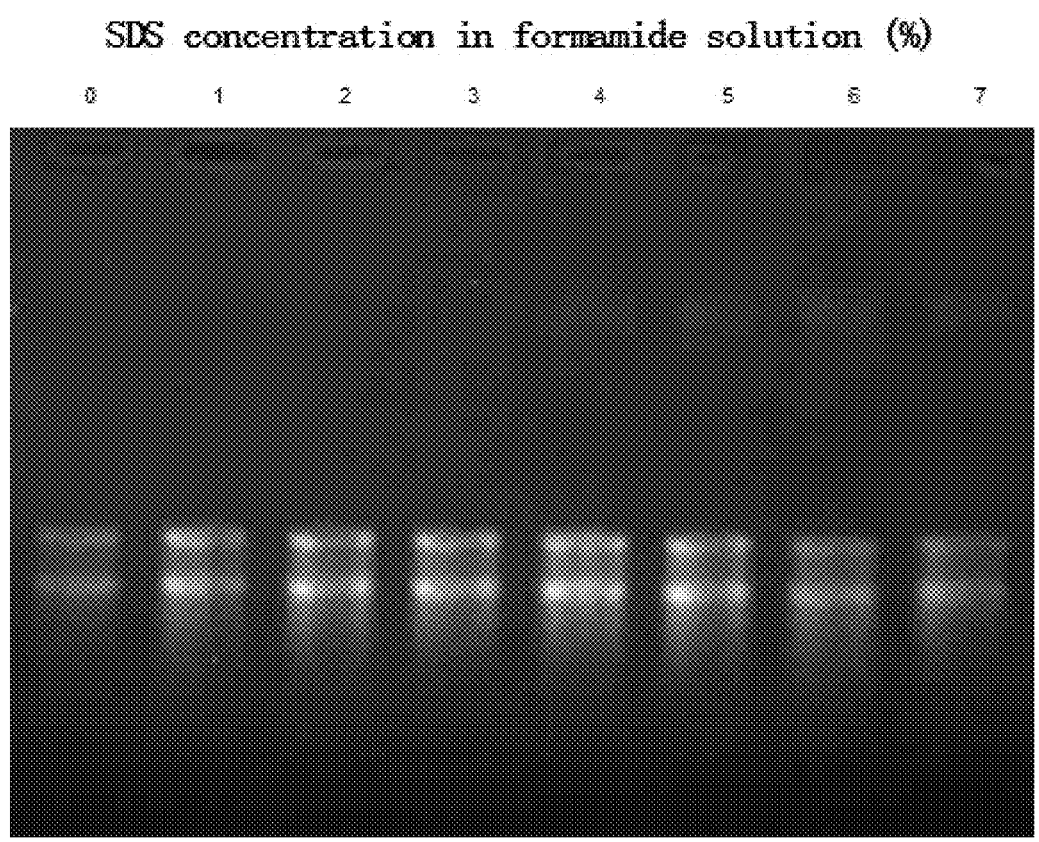
FIG. 2 is the product electropherogram, yield and purity ratio in Example 3.
Figure 2:
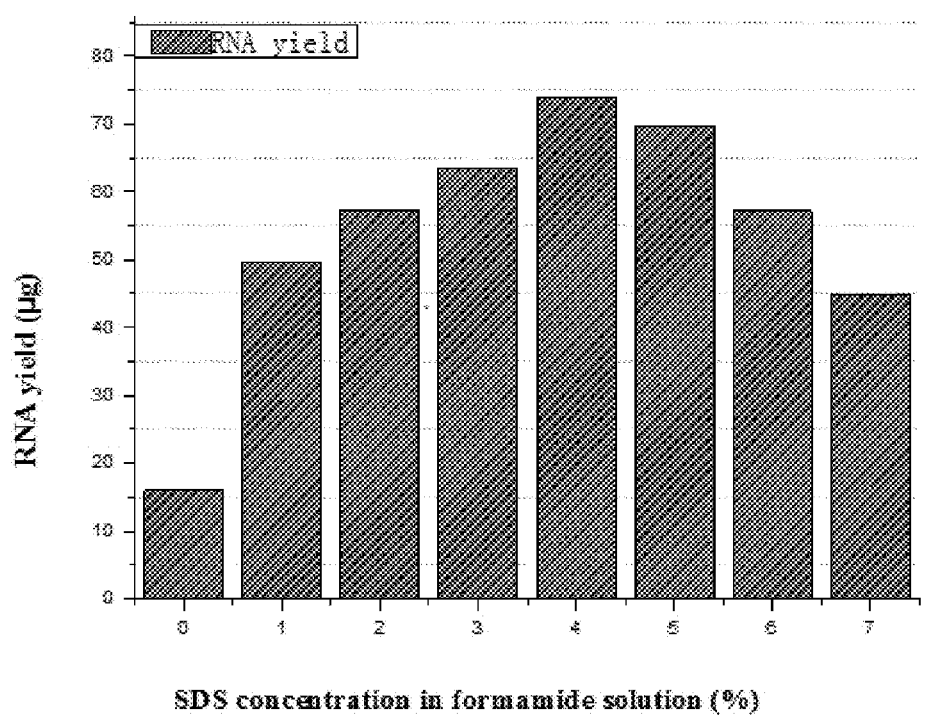

Results of agarose gel electrophoresis analysis: As shown in FIG. 2-1, all of the 23s rRNA and 16s rRNA from RNA samples are neatly edged, indicating that the RNA is not decomposed. In addition, the forth RNA band is the brightest, which shows that 4% of the SDS-formamide suspension is used for cell pyrolysis, and the maximum yield can be obtained.

Spectrophotometer: Add 75 µl RNA solution sample into the quartz cuvette which contains 2 ml TE solution (10 mM Tris-HCl, 1 mM EDTA, pH 8.0) and mix them. Take TE solution (10 mM Tris-HCl, 1 mM EDTA, PH8.0) as the control to measure the 260 nm, 280 nm absorbance by a ultraviolet spectrophotometer.

Figures 2, 3:
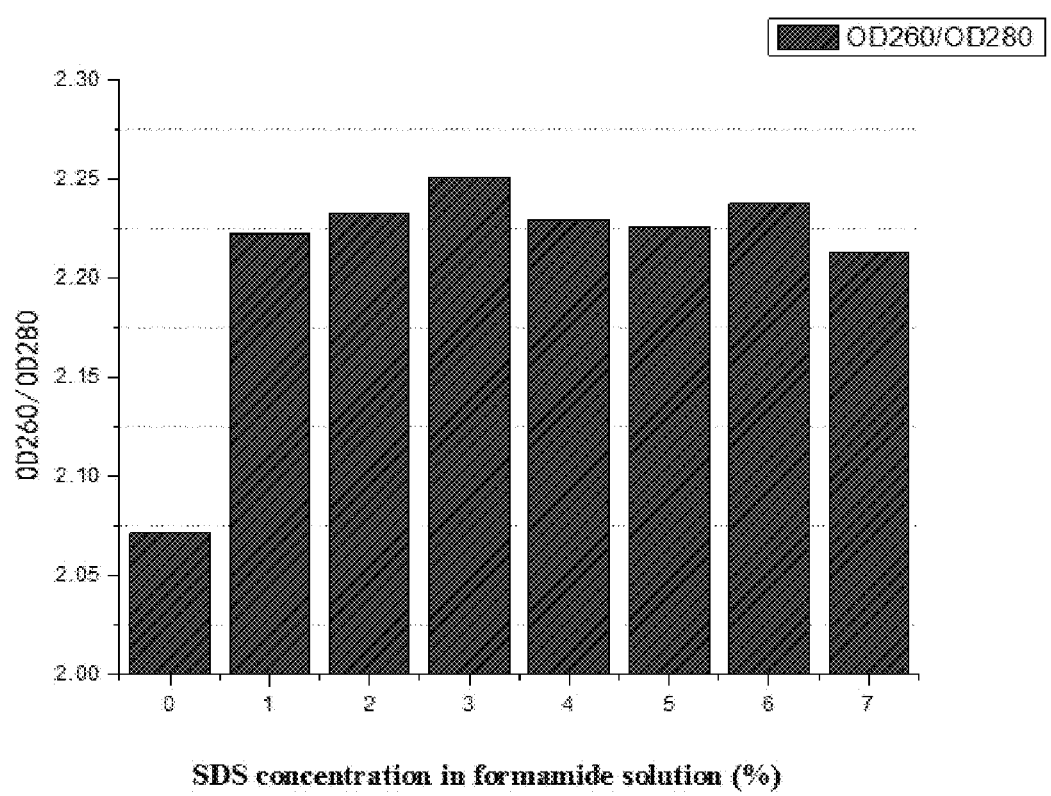
FIG. 3 is the product electropherogram, yield and purity ratio in Example 4.
Figures 1, 3:
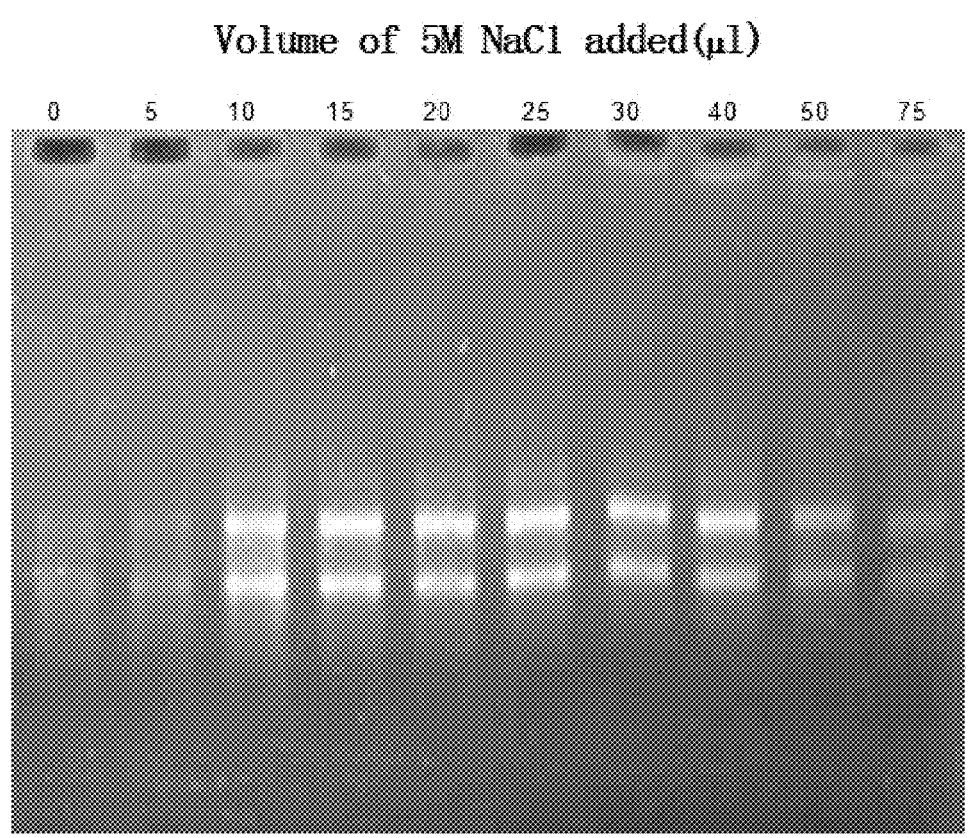
Figures 2, 3:
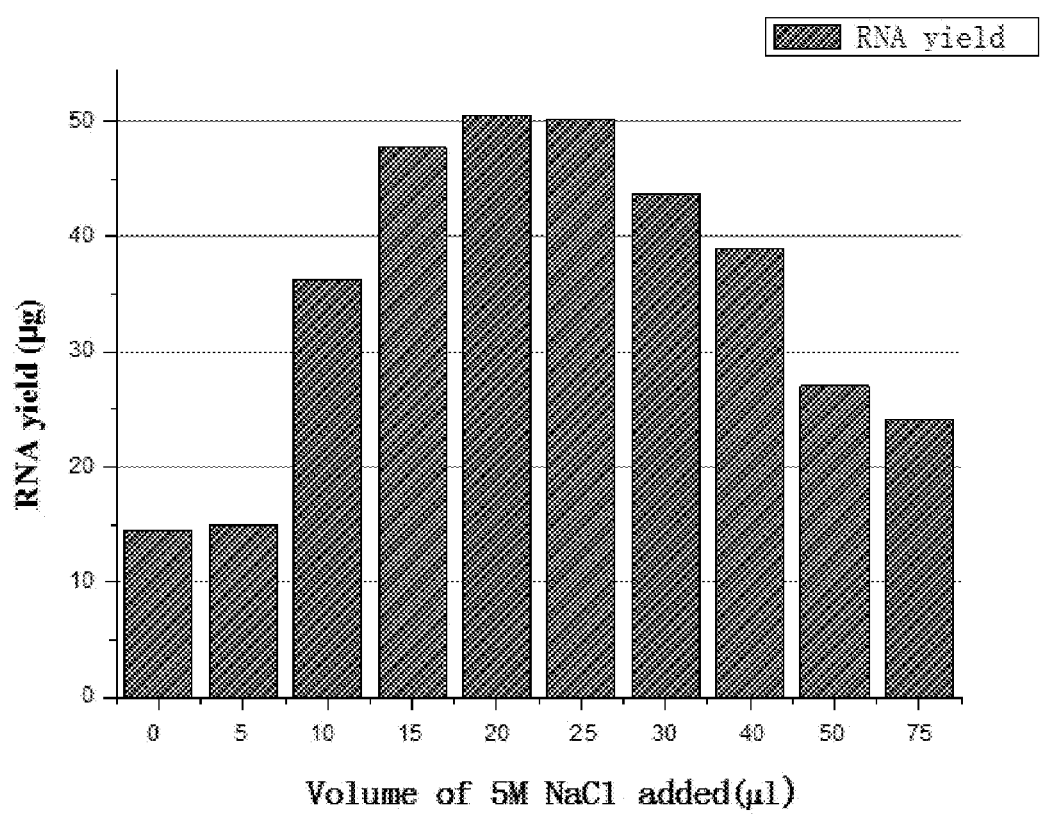
Figure 3:
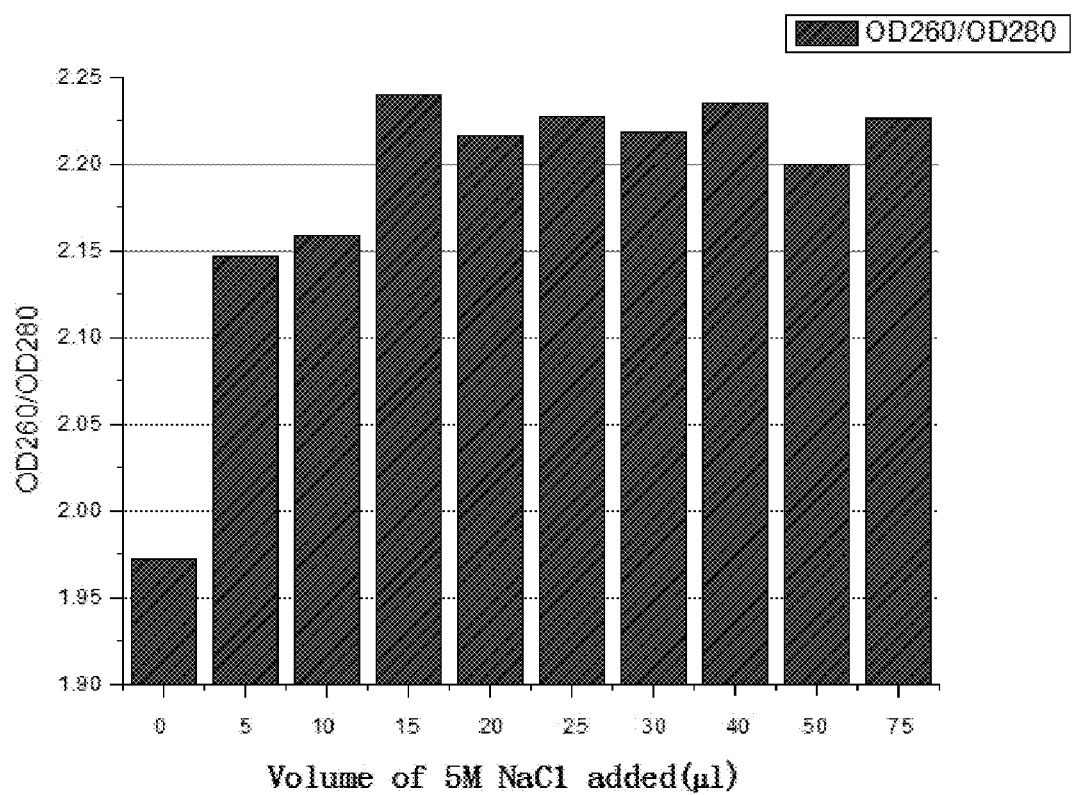

Spectrophotometer analysis: As shown in FIG. 2-2, RNA can also be produced without the presence of SDS; the effect of dissociation will get stronger with the increase of bivalent cation SDS concentration. The highest dissociation effect will be achieved by using 4.00% SDS cell Lysates. OD260/OD280 of all of the RNA samples are between 2.1-2.25 as shown in FIG. 2-3, which indicates that there is no protein contamination, no or only a very small amount of DNA contamination.

Summary of Example 3: This example illustrates the effect of SDS formamide solution of different concentrations in dissociating the *E. coli* cells and isolating the protein-RNA complexes at 80° C. The *E. coli* cells can be dissociated and protein-RNA complexes can be isolated (ie, dissociation role) at 80° C. by the formamide solution used to suspend *E. coli*; however, SDS can facilitate the process of dissociation; the maximum RNA yield can be obtained by using 4% SDS-formamide solution to suspend *E. coli* cells in the process of the 10-minute dissociation at 80° C.

Example 4

Sodium Ion (Na+) in the Formamide Facilitates the Separation of Protein-RNA Complexes The method for isolating and purifying RNA from biological material *Escherichia coli* strain ATCC27853 includes the following steps:

(1) Conduct overnight cultivation of the LB medium inoculated with *E. coli* strain ATCC27853 (purchased from Beijing DingGuo ChangSheng Biotechnology Co., Ltd.) in the shaker at 37° C. with 180 rev/min. Add 2 ml of the overnight cultivated broth to 100 ml LB medium which was insulated at 37° C. and then cultivate for 3 to 4 hours in the shaker at 37° C. with 180 rev/min and its 600 nm absorbance value will be about 0.8; add 1 ml *E. coli* culture broth to ten 1.5 ml centrifuge tubes respectively, after centrifugation at more than 8000 g for 1 min, discard the liquid; repeat the above process of centrifugation and absorb the residual liquid, thus the *E. coli* single cell precipitate is obtained.

Add 200 µl formamide respectively to each centrifuge tube which has the single cell precipitate and suspend at 0° C.;

(2) Add respectively to each centrifuge tube:

0 µl 5M NaCl (control group), 5 µl 5M NaCl, 10 µl 5M NaCl, 15 µl 5M NaCl, 20 µl 5M NaCl, 25 µl 5M NaCl, 30 µl 5M NaCl, 40 µl 5M NaCl, 50 µl 5M NaCl, 75 µl 5M NaCl, mix and incubate for 10 min at 80° C. to rupture the bacterial cells and then leave them at room temperature for 2 min;

(3) Add 700 µl 3.57M NaCl, 1.14 M KCl aqueous solution which has precipitation effect to the each of the product obtained in step (2), after vortex oscillation blending and centrifugation at 16000 g for 1 min at room temperature, pour this supernatant into another centrifuge tube;

(4) Add 500 µl isopropanol to the supernatant, mix it, after centrifugation at 12000 g for 2 min at 25° C., discard the upper phase liquid, the lower phase liquid and visible residual solid impurities between the upper and lower phase, thus the white RNA precipitate can be obtained at the bottom of the centrifuge tube.

Wash the white RNA precipitate using 1 ml aqueous ethanol solution with volume percentage concentration of 70%; after centrifugation at 16000 g at room temperature for 10 s, discard the washing liquid and dry the precipitate. Add 150 µl water for injection (without RNases contamination) to dissolve the precipitate.

Agarose gel electrophoresis: Same as the agarose gel electrophoresis method described in Example 1.

Results of agarose gel electrophoresis analysis: As shown in FIG. 3-1, 200 µl formamide solution and 10~50 µl 5M NaCl solution are used to suspend cell precipitate and the 23s rRNA and 16s rRNA bands obtained from RNA samples are neatly edged. Furthermore, a high yield of RNA can be obtained by using 200 µl formamide solution and 1050 µl 5M NaCl solution to suspend cell precipitate.

Spectrophotometer: Same as the method used in Example 3.

Spectrophotometer analysis: As shown in FIG. 3-2, a small amount of RNA can also be produced without the presence of NaCl; and the yield of E. coli RNA will be growing with the increase of the volume of 5M NaCl solution. The highest RNA yield will be achieved by using 200 μl formamide solution and 10 μl-50 μl 5M NaCl solution to suspend cell precipitate. OD260/OD280 of the RNA samples are all between 2.1-2.25 (as shown in FIG. 3-3), which indicates that there is no protein contamination, no or only a very small amount of DNA contamination.

Summary of Example 4: This example illustrates that 200 μl formamide solution and 10~50 μl 5M NaCl solution to suspend cell precipitate and incubate at 80° C. can dissociate the E. coli cells and achieve effective separation of the protein-RNA complexes, through which bare RNA molecules will be generated. The maximum yield of RNA can be achieved using 200 μl formamide solution and 20 μl 5M NaCl solution to suspend cell precipitate without protein and RNases contamination. It can be concluded through the comparison of the above results and the summary of Example 3 that sodium ion (Na+) in the formamide can effectively separate the bacterial protein-RNA complexes and generate complete bare RNA molecules.

Example 5

Extraction of RNA from the Mixture of Cabbage Leaves Formamide Homogenate and 5M NaCl (Dissociation Agent) of Different Volume The method for isolating and purifying RNA from biological materials includes the following steps:
(1) Add 3 ml formamide stored at 4° C. and 300 mg cabbage leaves (purchased from the market) to the Downce homogenizer on ice and homogenize for 20 s;
(2) Choose six 1.5 ml centrifuge tubes and add 200 μl cabbage leaves formamide homogenate to each one of them, and add 20 μl, 30 μl, 40 μl, 50 μl, 60 μl and 75 μl 5M NaCl aqueous solution to the tubes respectively at room temperature. After vortex oscillation blending, incubate the centrifuge tubes at 90° C. for 10 min and leave them at room temperature for 5 min.

Steps (3)~(4) are the same as described in Example 2.

Wash the white RNA precipitate using 1 ml aqueous ethanol solution with volume percentage concentration of 70%; after centrifugation at 16000 g at room temperature for 10 s, discard the washing liquid and dry the precipitate. Add 150 μl water for injection (without RNases contamination) to dissolve the precipitate.

Agarose gel electrophoresis: Same as the agarose gel electrophoresis method described in Example 1.

Figures 1, 4:
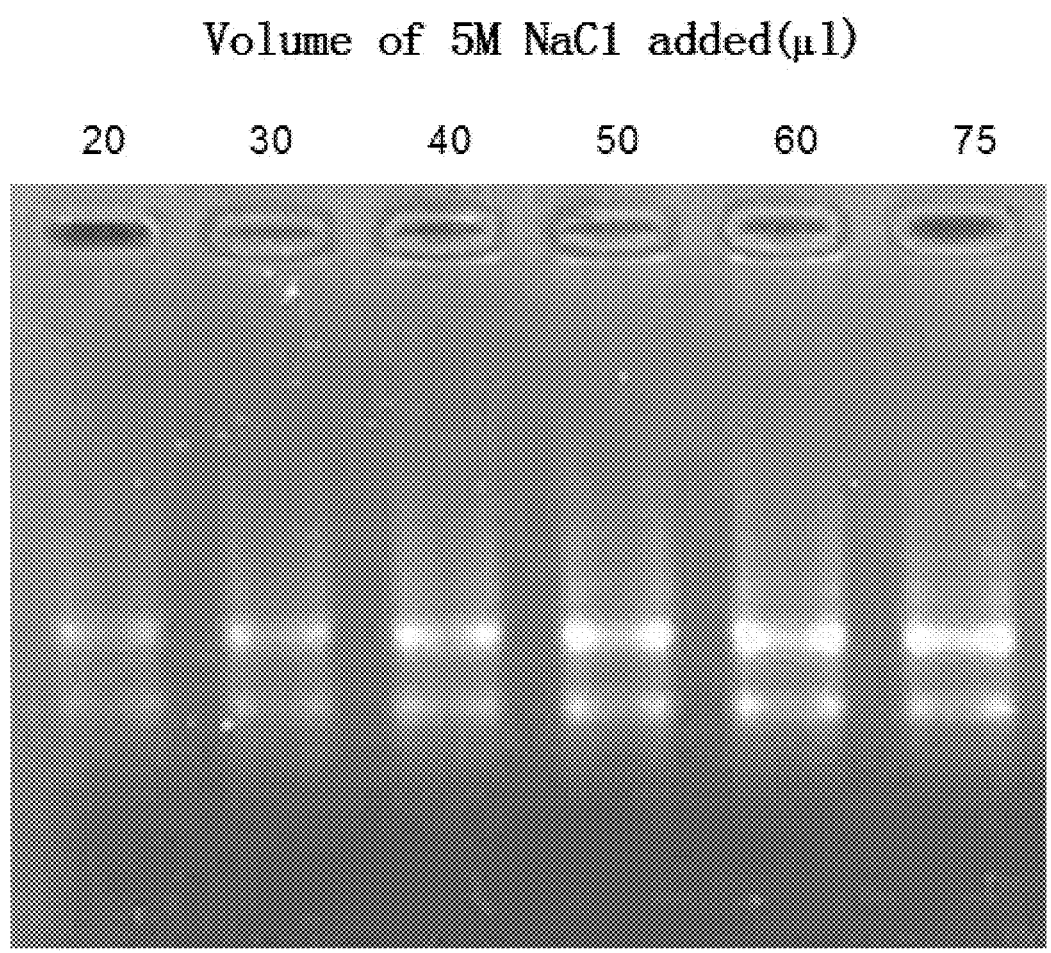
FIG. 4 is the product electropherogram, yield and purity ratio in Example 5.
Figures 2, 4:
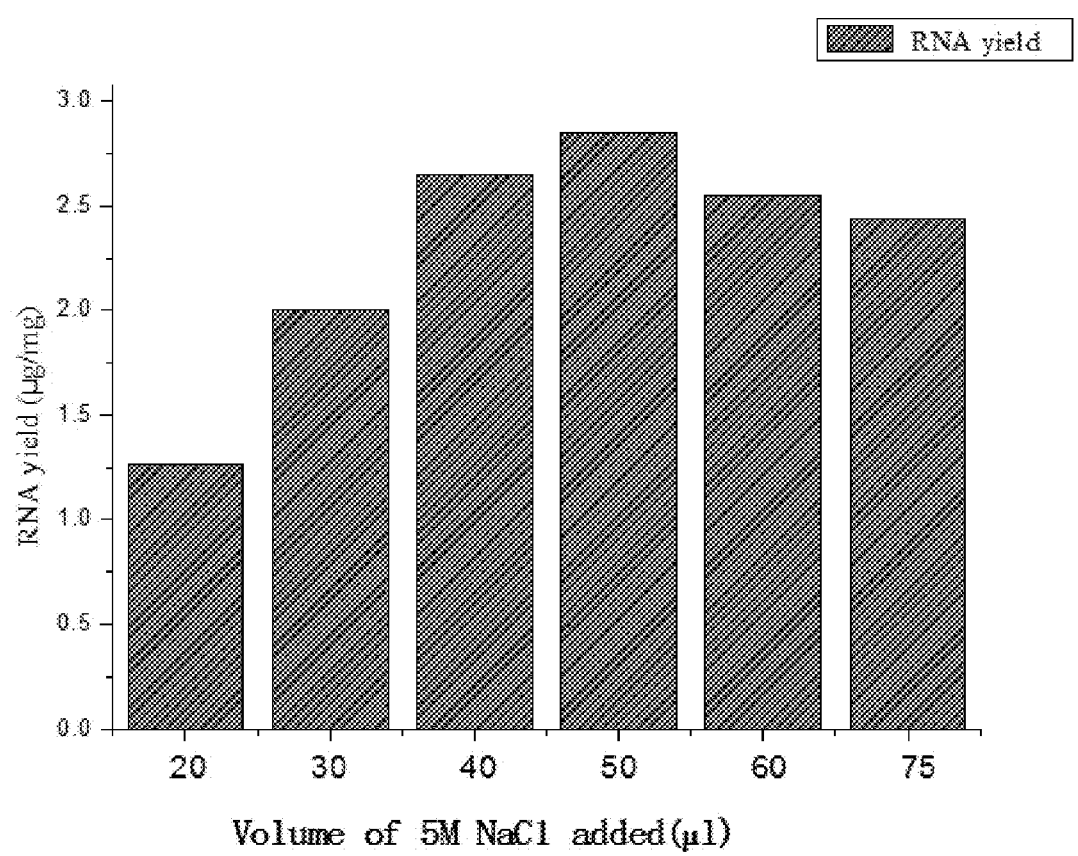
Figures 3, 4:
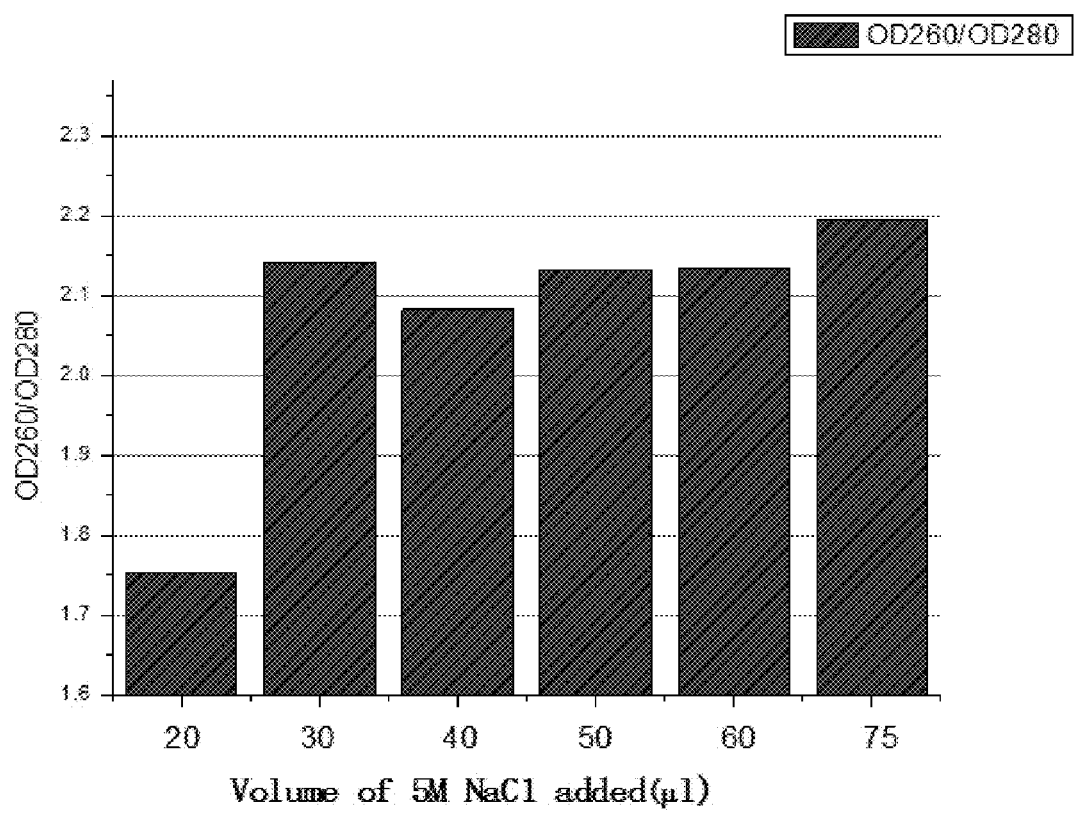

100 Results of agarose gel electrophoresis analysis: As shown in FIG. 4-1, 200 μl cabbage leaves formamide homogenate and 20~75 μl 5M NaCl solution are used to suspend cell precipitate and the 26s rRNA and 18s rRNA bands obtained from RNA samples are neatly edged and brightness ratio of them is close to 2:1. Furthermore, the RNA solution extracted from the mixture of 200 μl cabbage leaves formamide homogenate and 40~60 μl 5M NaCl solution has the brightest 18s rRNA and 26s rRNA electrophoresis band spectrum, i.e. it has the highest RNA yield.

Spectrophotometer: Same as the method used in Example 3.

Spectrophotometer analysis: As shown in FIG. 4-2, the extracted RNA yield of cabbage leaves will be growing with the increase of the 5M NaCl of the 200 μl cabbage leaves formamide homogenate. The maximum RNA yield will be achieved using 200 μl cabbage leaves formamide homogenate and 50 μl 5M NaCl solution to incubate at 90° C. OD260/OD280 of all of the RNA samples are between 2.1-2.25 (as shown in FIG. 4-3), which indicates that there is no protein contamination, no or only a very small amount of DNA contamination.

Summary of Example 5: This example illustrates that the eukaryotic cells protein-RNA complexes can be effectively separated and generate bare RNA molecules using 200 μl cabbage leaves formamide homogenate solution and 10~50 μl 5M NaCl aqueous solution to suspend cell precipitate and incubate at 90° C. The maximum RNA yield will be achieved without producing protein and RNases contamination through the use of 200 μl cabbage leaves formamide homogenate and 50 μl 5M NaCl solution to incubate at 90° C.

Example 6

Mouse Liver RNA Extraction (1)

The method for isolating and purifying RNA from biological materials includes the following steps:
(1) Add 2 ml formamide stored at 4° C. and 200 mg fresh mouse (Beijing White No. 1, purchased from Institute of Hematology, Chinese Academy of Medical Sciences) liver to the Downce homogenizer on ice and homogenize for 20 s;
(2) Add 200 μl mouse liver formamide homogenate solution and 50 μl 5M NaCl aqueous solution obtained from step (1) to the 1.5 ml centrifuge tube at room temperature. After vortex oscillation blending, incubate the centrifuge tubes at 90° C. for 10 min and leave them at room temperature for 2 min;
(3) Add 700 μl 3.57M NaCl, 1.14 M KCl aqueous solution which has precipitation effect to the 200 μl product obtained from step (2); after vortex oscillation blending and centrifugation at 16000 g for 5 min at room temperature, pour this supernatant into another centrifuge tube;
(4) Add 500 μl isopropanol to the supernatant, mix them; after centrifugation at 16000 g for 10 min at 25° C., discard the upper phase liquid, the lower phase liquid and visible residual solid impurities between the upper and lower phase; thus the white RNA precipitate can be obtained at the bottom of the centrifuge tube.

Wash the white RNA precipitate using 1 ml aqueous ethanol solution with volume percentage concentration of 70%; after centrifugation at 16000 g at room temperature for 10 s, discard the washing liquid and dry the precipitate. Add 150 μl water for injection (without RNases contamination) to dissolve the precipitate.

Agarose gel electrophoresis: Same as the agarose gel electrophoresis method described in Example 1.

Results of agarose gel electrophoresis analysis: The 28s rRNA and 18s rRNA bands obtained from RNA samples are neatly edged and the brightness ratio of them is close to 2:1.

Spectrophotometer: Same as the method used in Example 3.

Spectrophotometer analysis: The yield of the extracted RNA of mouse liver is 5.2 μg/mg and the ratio of the 260 nm and 280 nm absorbance of the obtained RNA solution is 2.22.

Summary of Example 6: RNA of the animal tissue can be effectively extracted using this method.

Example 7

Mouse Liver RNA Extraction (2)

The method for isolating and purifying RNA from biological materials includes the following steps:

Steps (1)~(4) are the same as described in Example 6.

Wash the white RNA precipitate using 1 ml aqueous ethanol solution with volume percentage concentration of 70%; after centrifugation at 16000 g at room temperature for 10 s, discard the washing liquid, then put the centrifuge tube on the filter paper to dry the precipitate; add 1 ml aqueous ethanol solution with volume percentage concentration of 95% to soak the RNA precipitate; after soaking the covered centrifuge tube for 30 days, conduct centrifugation and discard the ethanol solution with volume percentage concentration of 95%, then put the centrifuge tube on the filter paper to dry the RNA precipitate; finally 150 µl water for injection (without RNases contamination) is added to dissolve the precipitate.

Agarose gel electrophoresis: Same as the agarose gel electrophoresis method described in Example 1.

Results of agarose gel electrophoresis analysis: The 28s rRNA and 18s rRNA bands obtained from RNA samples are neatly edged and the brightness ratio of them is close to 2:1. This result is close to the result of spectrophotometer analysis in Example 6.

Spectrophotometer: Same as the method used in Example 3.

Spectrophotometer analysis: The yield of the extracted RNA of mouse liver is 5.4 µg/mg and the ratio of the 260 nm and 280 nm absorbance of the obtained RNA solution is 2.24. This result is close to the result of spectrophotometer analysis in Example 6.

Summary of Example 7: The RNA precipitate extracted using the method in this invention cannot be decomposed even being stored in aqueous ethanol solution with volume percentage concentration of 95% at room temperature.

Example 8

Mouse Liver RNA Extraction (3)

The method for isolating and purifying RNA from biological materials includes the following steps:
(1) Add the mixture of 2 ml formamide stored at 4° C. and 0.5 ml 5M NaCl aqueous solution to the Downce homogenizer on ice and mix them, then add 200 mg of fresh mouse (Beijing White No. 1) liver and homogenize for 1 min.
(2) Add 250 µl mouse liver formamide homogenate solution which is obtained in step (1) to the 1.5 ml centrifuge tube at room temperature, incubate the centrifuge tubes at 90° C. for 10 min and leave them at room temperature for 2 min;

Steps (3)~(4) are the same as described in Example 6.

Wash the white RNA precipitate using 1 ml aqueous ethanol solution with volume percentage concentration of 70%; after centrifugation at 16000 g at room temperature for 10 s, discard the washing liquid and dry the precipitate. Add 150 µl water for injection (without RNases contamination) to dissolve the precipitate.

Spectrophotometer: Same as the method used in Example 3.

Spectrophotometer analysis: The yield of the extracted RNA of mouse liver is 4.95 µg/mg and the ratio of the 260 nm and 280 nm absorbance of the obtained RNA solution is 2.15; this result is close to the result of spectrophotometer analysis in Example 6.

Agarose gel electrophoresis: Same as the agarose gel electrophoresis method described in Example 1.

Results of agarose gel electrophoresis analysis: The 28s rRNA and 18s rRNA bands obtained from RNA samples are neatly edged and the brightness ratio of them is close to 2:1. This result is close to the result of spectrophotometer analysis in Example 6.

Summary of Example 8: High quality and high yield of RNA sample can also be obtained by extracting RNA through homogenization of the mouse liver using formamide and 5M NaCl aqueous solution at 4:1 in volume.

Example 9

Extraction of RNA from Mouse Intestine

The method for isolating and purifying RNA from biological materials includes the following steps:
(1) Add 1 ml formamide stored at 4° C. and 100 mg fresh and physiological saline washed mouse (Beijing White No. 1) intestine to the 1.5 ml centrifuge tube. Three times of homogenizing (20000 rpm, 20 seconds each time) using the electrophoresis homogenizer at 37° C.;

Step (2) is the same as described in Example 6;
(3) Add 700 µl 3.57M NaCl, 1.14 M KCl aqueous solution which has precipitation effect to the 200 µl product obtained in step (2); after vortex oscillation blending and centrifugation at 2000 g for 30 min at room temperature, pour this supernatant into another centrifuge tube;

Step (4) is the same as described in Example 6.

Wash the white RNA precipitate using 1 ml aqueous ethanol solution with volume percentage concentration of 70%; after centrifugation at 16000 g at room temperature for 10 s, discard the washing liquid and dry the precipitate. Add 100 µl water for injection (without RNases contamination) to dissolve the precipitate.

Agarose gel electrophoresis: Same as the agarose gel electrophoresis method described in Example 1.

Results of agarose gel electrophoresis analysis: The 28s rRNA and 18s rRNA bands obtained from RNA samples are neatly edged and the brightness ratio of them is close to 2:1.

Spectrophotometer: Same as the method used in Example 3.

Spectrophotometer analysis: The yield of the extracted RNA of mouse intestine is 1.21 µg/mg and the ratio of the 260 nm and 280 nm absorbance of the obtained RNA solution is 2.22.

Summary of Example 9: RNA of mouse intestine can be effectively extracted using the method in this invention.

Example 10

The Relationship Between the Dissociation Time Using 5M NaCl and RNA Yield of Rape Leaves The method for isolating and purifying RNA from biological materials includes the following steps:
(1) Add 5 ml formamide stored at 4° C. and 500 mg fresh rape (*Brassica campestris* L.) leaves to the Downce homogenizer on ice and fully homogenize them;
(2) Add 200 µl rape leaves formamide homogenate and 50 µl 5M NaCl aqueous solution to seven 1.5 ml centrifuge tubes respectively at room temperature. After vortex oscillation blending, incubate the centrifuge tubes for 1, 2, 5, 10, 15, 20 and 30 minutes respectively. Then leave them at room temperature for 2 min.

Steps (3)~(4) are the same as described in Example 6.

Wash the white RNA precipitate using 1 ml aqueous ethanol solution with volume percentage concentration of 70%; after centrifugation at 16000 g for 10 s at room temperature, discard the washing liquid and dry the precipitate. Add 100 μl water for injection (without RNases contamination) to dissolve the precipitate.

Spectrophotometer: Same as the method used in Example 3.

Figure 5:
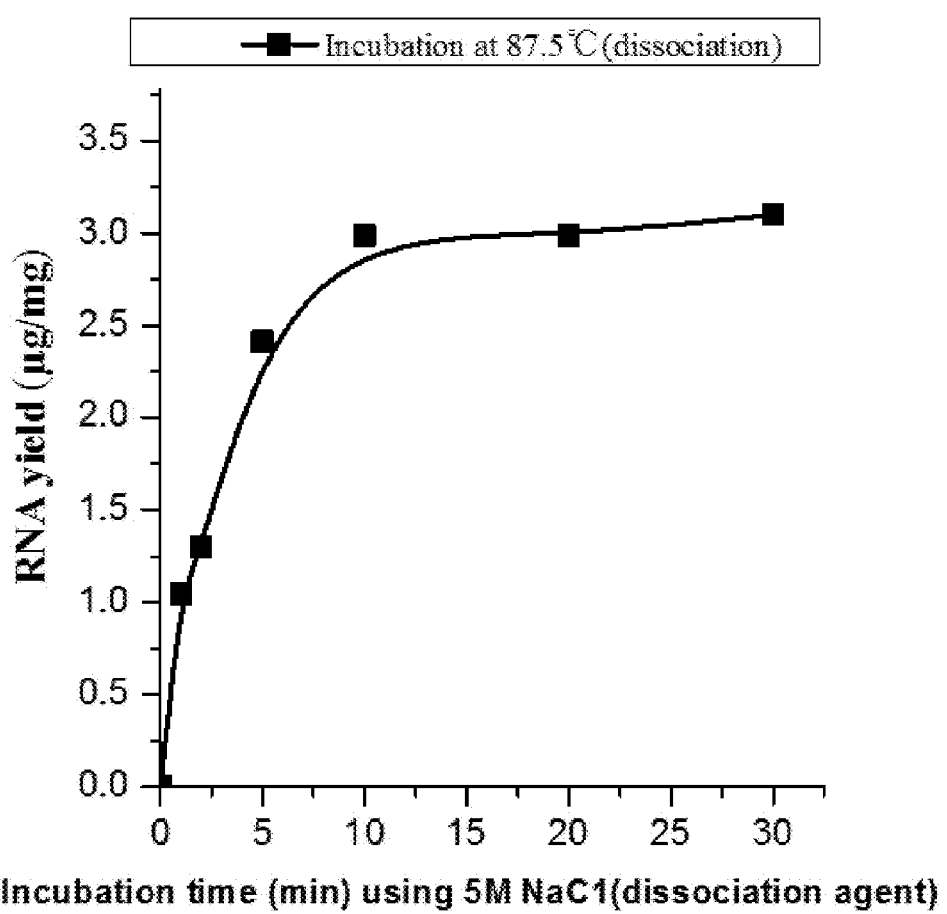
FIG. 5 shows the relationship between the dissociation time using 5M NaCl aqueous solution and RNA yield of rape leaves in Example 10.

Spectrophotometer analysis: As shown in FIG. 5, the yield of the extracted RNA of rape leaves will be increasing with the growth of incubation time. And the RNA yield will be close to the maximum level when the time of incubation reaches 10 min.

Summary of Example 10: After 10 min of incubation (dissociation), the RNA yield will be close to the maximum level when 5M NaCl aqueous solution is used as dissociation agents to extract RNA.

Example 11

The Relationship Between the Volume of 13.5M LiCl Aqueous Solution Used for Dissociation and RNA Yield of Hawthorn Leaves The method for isolating and purifying RNA from biological materials includes the following steps:
(1) Add 7 ml formamide stored at 4° C. and 700 mg fresh hawthorn (*Crataegus pinnatifida*) leaves to the Downce homogenizer on ice and fully homogenize them;
(2) Prepare three groups of 1.5 ml centrifuge tubes with 9 tubes in each one of them. Add 200 μl hawthorn leaves formamide homogenate and 0 μl, 4 μl, 7 μl, 9 μl, 10 μl, 11 μl, 15 μl, 20 μl and 25 μl 13.5M LiCl aqueous solution to the 9 centrifuge tubes of the three groups respectively at room temperature. After vortex oscillation blending, incubate the three groups of centrifuge tubes at 55° C., 75° C. and 85° C. respectively for 2 min. Then leave them at room temperature for 2 min.

Steps (3)~(4) are the same as described in Example 6.

Wash the white RNA precipitate using 1 ml aqueous ethanol solution with volume percentage concentration of 70%; after centrifugation at 16000 g for 10 s at room temperature, discard the washing liquid and dry the precipitate. Add 100 μl water for injection (without RNases contamination) to dissolve the precipitate.

Spectrophotometer: Same as the method used in Example 3.

Figure 6:
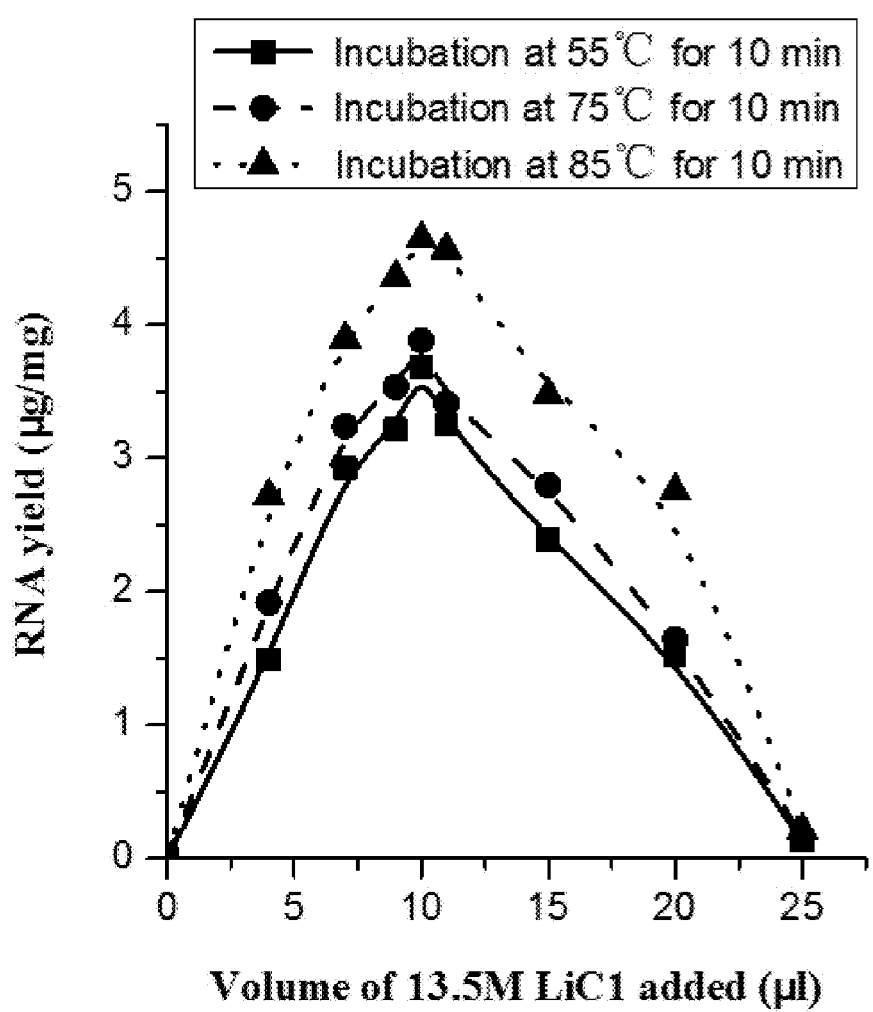
FIG. 6 shows the relationship between the volume of 13.5M LiCl aqueous solution used for dissociation and RNA yield of hawthorn leaves in Example 11.

Spectrophotometer analysis: As shown in FIG. 6, when extracting RNA of hawthorn leaves at different temperature of incubation (dissociation), the maximum yield of RNA can be achieved using the mixture of 10 μl 13.5M LiCl aqueous solution and 200 μl leaf homogenate for dissociation.

Summary of Example 11: The maximum of RNA yield can be achieved using the mixture of 13.5M LiCl aqueous solution and hawthorn leaves homogenate with the volume ratio of 1:20 to incubate (dissociate) at a certain temperature.

Example 12

The Relationship Between the Dissociation Time Using 13.5M LiCl Aqueous Solution and RNA Yield of Hawthorn Leaves (1) Add 7 ml formamide stored at 4° C. and 700 mg fresh hawthorn (*Crataegus pinnatifida*) leaves to the Downce homogenizer on ice and fully homogenize them;
(2) Prepare three groups of 1.5 ml centrifuge tubes with 6 tubes in each one of them. Add 200 μl hawthorn leaves formamide homogenate and 10 μl 13.5 M LiCl (dissociation agents) to the 6 centrifuge tubes of the three groups respectively at room temperature. After vortex oscillation blending, incubate the three groups of centrifuge tubes at 55° C., 75° C. and 85° C. for 0, 1 min, 2 min, 5 min, 10 min and 20 min respectively. Then leave them at room temperature for 2 min.

Steps (3)~(4) are the same as described in Example 6;

Wash the white RNA precipitate using 1 ml aqueous ethanol solution with volume percentage concentration of 70%; after centrifugation at 16000 g for 10 s at room temperature, discard the washing liquid and dry the precipitate. Add 100 μl water for injection (without RNases contamination) to dissolve the precipitate.

Spectrophotometer: Same as the method used in Example 3.

Figure 7:
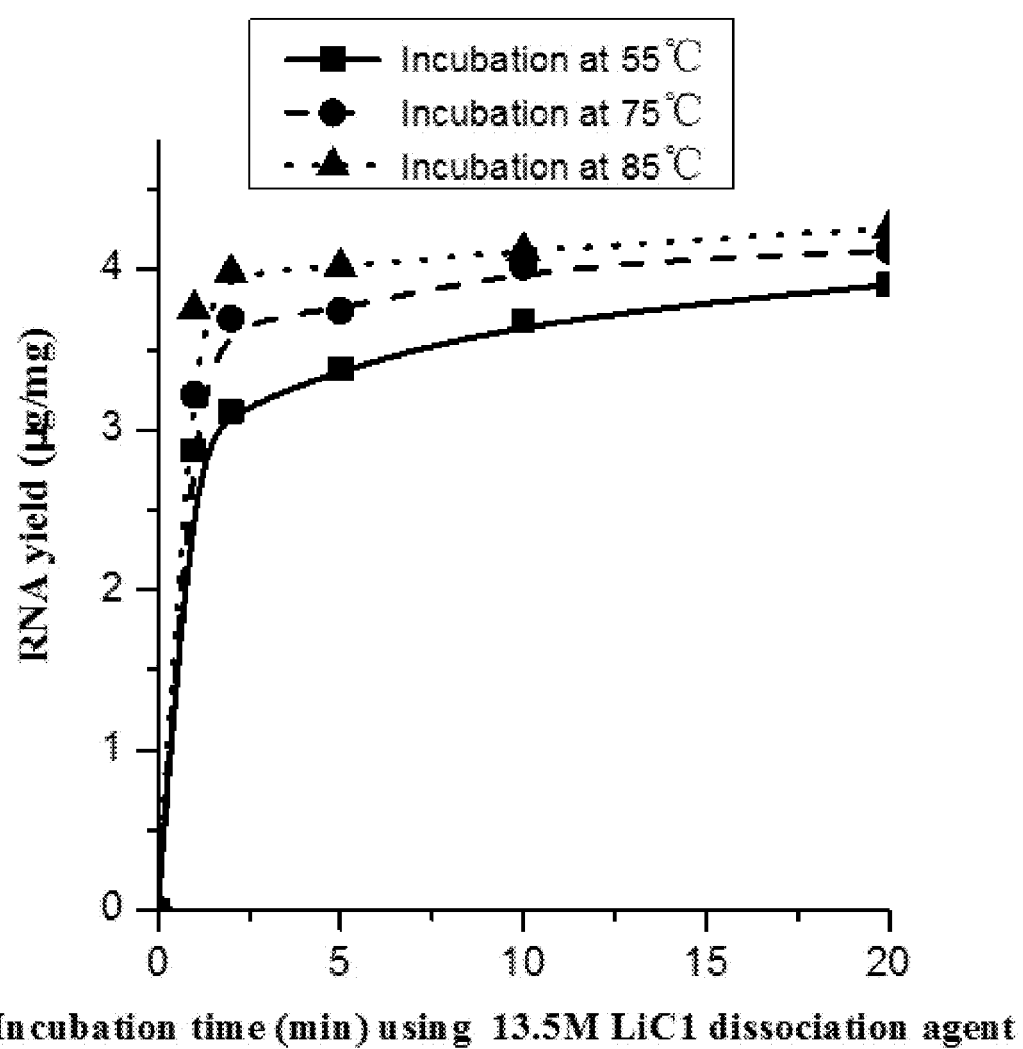
FIG. 7 shows the relationship between the dissociation time using 13.5M LiCl aqueous solution and RNA yield of hawthorn leaves in Example 12.

Spectrophotometer analysis: As shown in FIG. 7, when extracting RNA of hawthorn leaves at different temperature of incubation (dissociation), the yield of the extracted RNA of hawthorn leaves will be increasing with the growth of incubation time. And the RNA yield will be close to the maximum level when the time of incubation reaches 2 min.

Summary of Example 12: After 2 min of incubation (dissociation), the RNA yield will be close to the maximum level when 13.5M LiCl aqueous solution is used to extract RNA at different temperatures of incubation (dissociation).

Example 13

The Relationship Between the Dissociation Temperature Using 13.5M LiCl Aqueous Solution and RNA Yield of Poplar Leaves (1) Add 7 ml formamide stored at 4° C. and 700 mg fresh poplar (*Populus bonatii* Levi) leaves to the Downce homogenizer on ice and fully homogenize them;
(2) Add 200 μl poplar leaves formamide homogenate and 10 μl 13.5 M LiCl aqueous solution to eight 1.5 ml centrifuge tubes respectively at room temperature. After vortex oscillation blending, incubate the centrifuge tubes respectively at 29° C., 37° C., 45° C., 55° C., 65° C., 75° C., 85° C. and 95° C. for 2 min;

Steps (3)~(4) are the same as described in Example 6;

Wash the white RNA precipitate using 1 ml aqueous ethanol solution with volume percentage concentration of 70%; after centrifugation at 16000 g at room temperature for 10 s, discard the washing liquid and dry the precipitate. Add 100 μl water for injection (without RNases contamination) to dissolve the precipitate.

Agarose gel electrophoresis: Same as the agarose gel electrophoresis method described in Example 1.

Results of agarose gel electrophoresis analysis: The bands of 26s rRNA and 18s rRNA of the RNA incubated (dissociated) at 29~85° C. are neatly edged, which indicate that it is not decomposed. But the bands of 26s rRNA and 18s rRNA of the RNA incubated (dissociated) at 95° C. are not neatly edged, which indicates that the RNA sample has already been decomposed.

Spectrophotometer: Same as the method used in Example 3.

Figure 8:
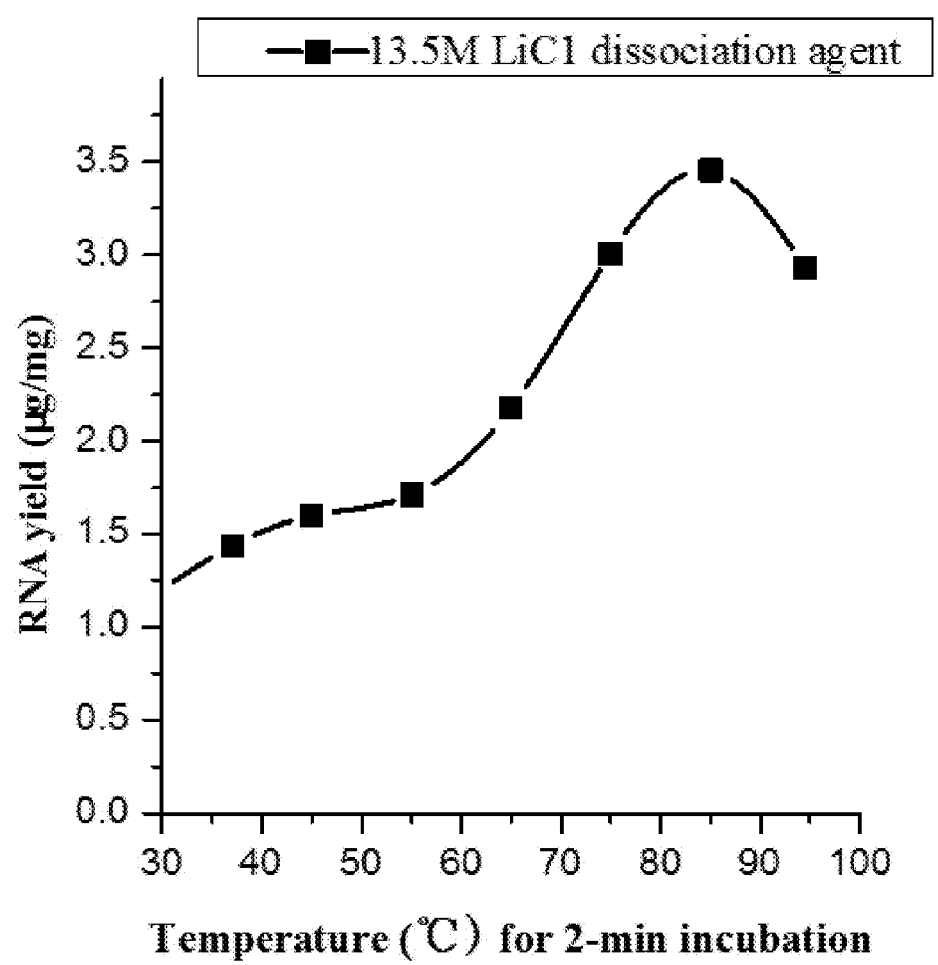
FIG. 8 shows the relationship between the dissociation temperature using 13.5M LiCl aqueous solution and RNA yield of poplar leaves in Example 13.

Spectrophotometer analysis: As shown in FIG. 8, when extracting RNA of poplar leaves at different temperature of incubation (dissociation), the yield of the extracted RNA of poplar leaves will be increasing with the growth of incubation temperature. And the RNA yield will be close to the maximum level when the temperature of incubation (dissociation) reaches 85° C.

Summary of Example 13: When 13.5M LiCl aqueous solution is used to extract RNA at different temperatures of incubation (dissociation), the RNA yield is close to the maximum level when the temperature of incubation (dissociation) reaches 85° C. and the RNA has not been decomposed in the process.

Example 14

The Relationship Between the Cooling Time after the Dissociation of Rape Leaves Homogenate and the RNA Yield (1) Add 7 ml formamide stored at 4° C. and 700 mg fresh rape (*Brassica campestris* L.) leaves to the Downce homogenizer on ice and fully homogenize them;
(2) Prepare two groups of 1.5 ml centrifuge tubes with four tubes in each one of them. Add 200 μl rape leaves formamide homogenate and 50 μl 5 M NaCl aqueous solution to the four centrifuge tubes of the two groups respectively at room temperature. After vortex oscillation blending, incubate the two groups of centrifuge tubes respectively at 90° C. for 10 min. Then leave them at room temperature or place them in ice for 0 min, 2 min, 5 min and 10 min respectively.

Steps (3)~(4) are the same as described in Example 6;
Wash the white RNA precipitate using 1 ml aqueous ethanol solution with volume percentage concentration of 70%; after centrifugation at 16000 g at room temperature for 10 s, discard the washing liquid and dry the precipitate. Add 100 μl water for injection (without RNases contamination) to dissolve the precipitate.

Spectrophotometer: Same as the method used in Example 3.

Figure 9:
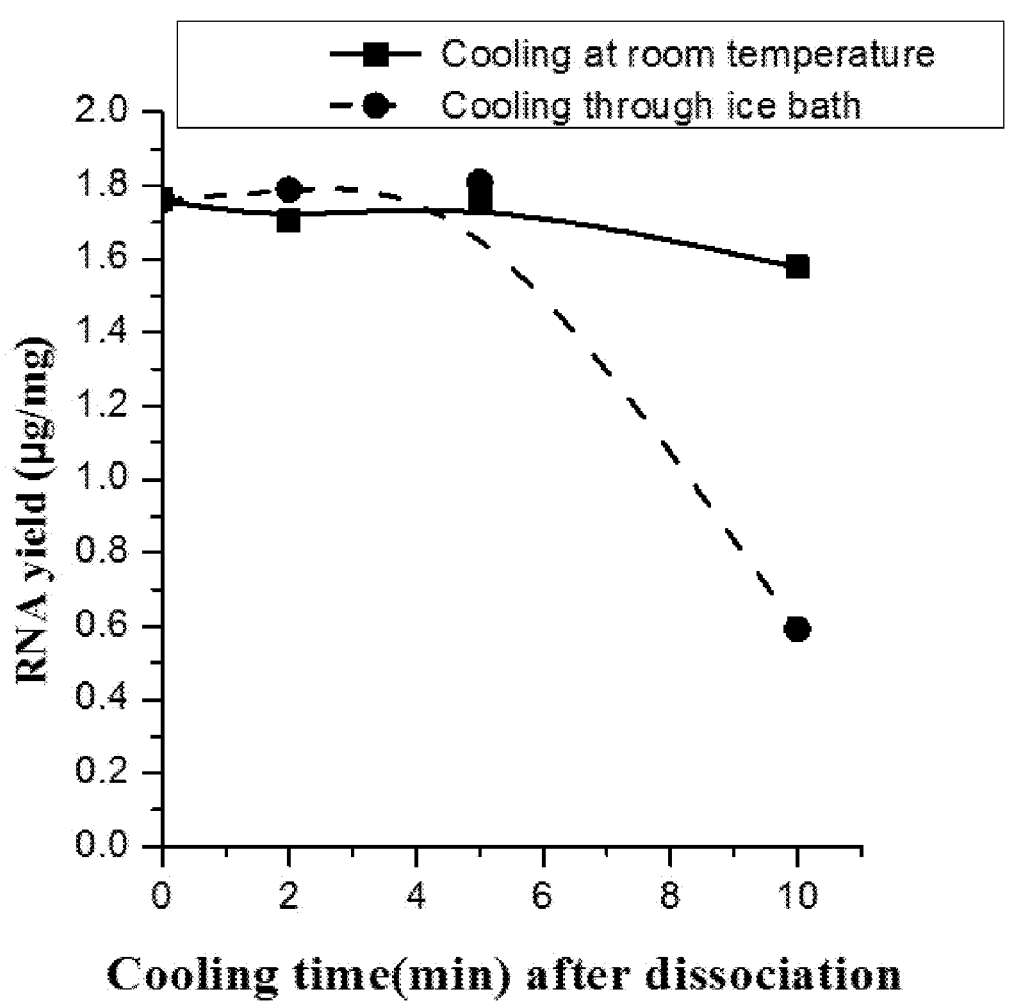
FIG. 9 shows the relationship between cooling time after the rape leaves homogenate solutions dissociation and RNA yields in Example 14.

Spectrophotometer analysis: As shown in FIG. 9, the yield of the extracted RNA decreased because of the homogenized mixture is kept for a long time after dissociation; there will be very little decrease of the yield of the extracted RNA if the homogenized mixture is kept for only 5 min after dissociation; if the dissociation is conducted at low temperatures (e.g. 0° C.), the cooling process after it will be more easily lead to a decrease in the yield of RNA.

Summary of Example 14: After the effect of dissociation, it is not advisable to keep the homogenized mixture for more than 5 min; it is better to keep it at room temperature (25° C.).

Example 15

Comparison of RT-PCR Amplification of β-Actin mRNA Extracted from the Mouse Liver RNA Samples Using this Method and the Trizol Reagent Method Respectively 1. Extraction of mouse (Beijing White No. 1) liver RNA as described in step (1)-(4) of Example 6; wash the white RNA precipitate using 1 ml aqueous ethanol solution with volume percentage concentration of 70%; after centrifugation at 16000 g for 10 s at room temperature, discard the washing liquid and dry the precipitate. Add 50 μl water for injection (without RNases contamination) to dissolve about 20 mg of the precipitate of the mouse liver RNA.
2. Extracting 50 mg of mouse liver RNA according to the Trizol manual from Invitrogen and dissolving the obtained RNA precipitate in 50 μl water (without RNases contamination);
3. The first cDNA in the above mentioned two RNA samples was synthesized by using AMV reverse transcriptase according to the manual of KaTaRa;
4. cDNA synthesis solution and a variety of solution are added as shown in the following table; wherein the primer f and primer r as listed below are a pair of primers used for amplification of the cDNA of β-actin:

β-actin F 5'atcatgtttgagaccttcaaca 3';

β-actin R5'catctcttgctcgaagtcca 3';

The length of the amplified DNA product is 318 bp;
Amplification conditions are as follows: Initial denaturation at 94° C. for 2 min; denaturation of 35 cycles for 30 s at 94° C., quenching for 30 s at 62° C. and extension reaction for 30 s at 72° C.; termination of the extension reaction for 2 min at 72° C.

TABLE 1

| Composition | Volume/ul |
| --- | --- |
| cDNA | 2 |
| 10× PCR Buffer | 2.5 |
| dNTPs (10 mM) | 0.5 |
| Primer f (20 pmol/ul) | 0.25 |
| Primer r (20 pmol/ul) | 0.25 |
| Taq enzyme (2 u/ul) | 0.5 |
| Sybr Green I (10×) | 1 |
| ddH2O | 18 |

Agarose gel electrophoresis: 1 μl of the above RT-PCR amplification product was electrophoresed in 1.2% non-denaturing agarose the gel (1×TAE electrophoresis buffer).

Figure 10:
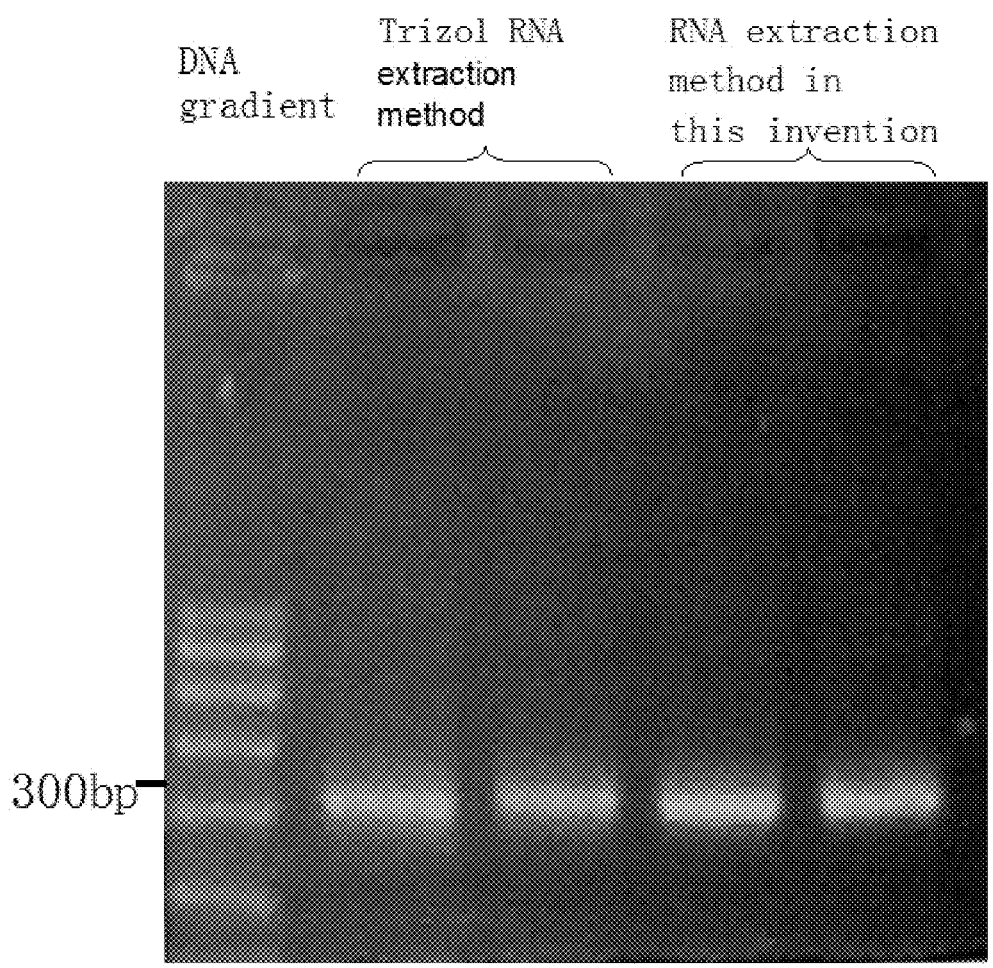
FIG. 10 shows the comparison of RT-PCR amplification of β-actin mRNA extracted from the mouse liver RNA samples using this method and the Trizol reagent method respectively in Example 15.

Results of agarose gel electrophoresis analysis: As shown in FIG. 10, the method in this invention is used for β-actin-mRNA amplification of RNA samples obtained from about 20 mg in mouse liver, and the comparison between the obtained DNA product pieces and the DNA product fragment obtained from the 50 mg mouse liver RNA samples using Trizol reagent method shows that the brightness of the former is twice that of the latter.

Example 16

Comparison of RT-PCR Amplification of β-Actin mRNA Extracted from the Rape Leaves RNA Samples Using this Method and the Trizol Reagent Method Respectively 1. Extraction of rape (*Brassica campestris* L.) leaves RNA as described in step (1)-(4) of Example 14; Wash the white RNA precipitate by using 1 ml aqueous ethanol solution with volume percentage concentration of 70%; after centrifugation at 16000 g at room temperature for 10 s, discard the washing liquid and dry the precipitate. Add 50 μl water for injection (without RNases contamination) to dissolve about 20 mg of the precipitate of the rape leaves RNA.
2. Extracting 50 mg of rape leaves RNA according to the Trizol manual from Invitrogen and dissolving the obtained RNA precipitate in 50 μl water (without RNases contamination);
3. The first cDNA in the above mentioned two RNA samples is synthesized using AMV reverse transcriptase according to the manual of KaTaRa;
208. cDNA synthesis solution and a variety of solution are added as shown in the following table; wherein the primer f and primer r as listed below are a pair of primers used for amplification of the cDNA of β-actin:

β-actin F 5'ggaatggtgaaggctggtt 3';

β-actin R5'tcccgttctgcggtagtg 3';

The length of the amplified DNA product is 318 bp;

Amplification conditions are as follows: Initial denaturation at 94° C. for 2 min; denaturation of 35 cycles for 30 s at 94° C., quenching for 30 s at 62° C. and extension reaction for 30 s at 72° C.; termination of the extension reaction for 2 min at 72° C.

TABLE 2

| Composition | Volume/ul |
|---|---|
| cDNA | 2 |
| 10× PCR Buffer | 2.5 |
| dNTPs (10 mM) | 0.5 |
| Primer f (20 pmol/ul) | 0.25 |
| Primer r (20 pmol/ul) | 0.25 |
| Taq enzyme (2 u/ul) | 0.5 |
| Sybr Green I (10×) | 1 |
| ddH2O | 18 |

Agarose gel electrophoresis: 1 μl of the above RT-PCR amplification product is electrophoresed in 1.2% non-denaturing agarose the gel (1×TAE electrophoresis buffer).

Figure 11:
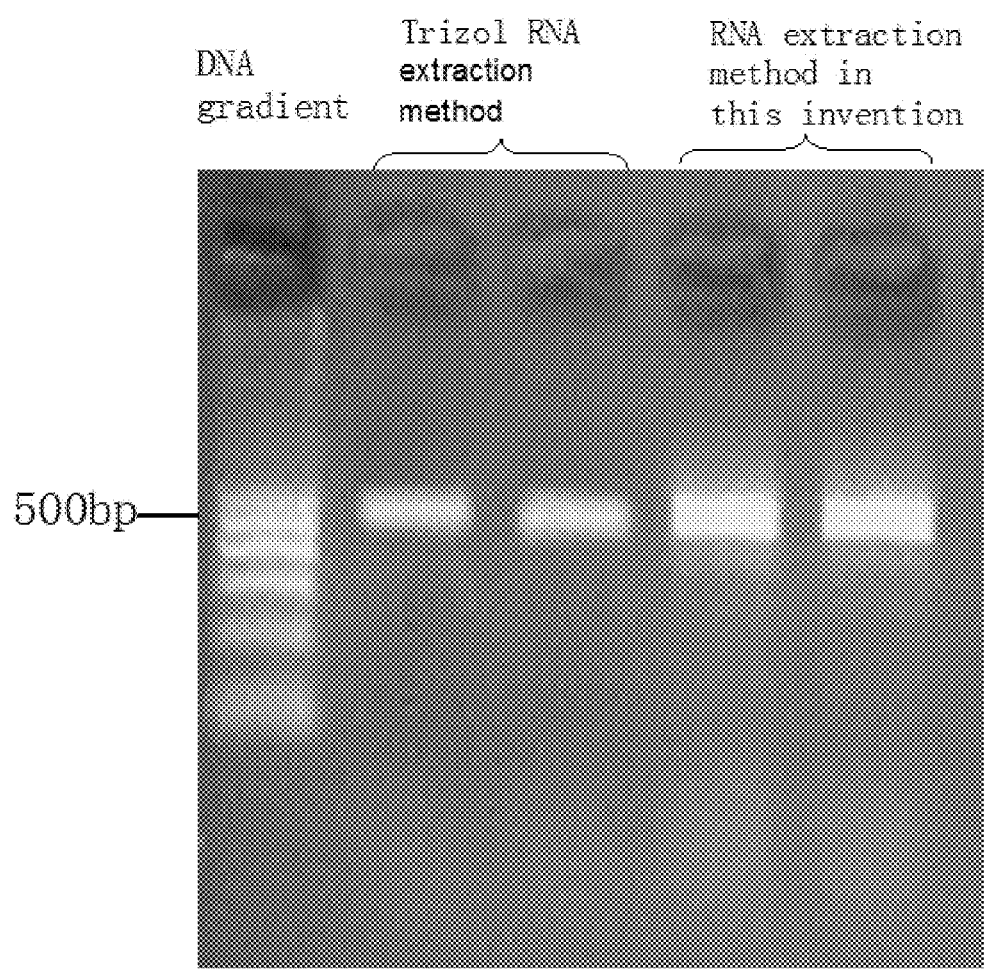
FIG. 11 shows the comparison of RT-PCR amplification of β-actin mRNA extracted from the rape leaves RNA samples using this method and the Trizol reagent method respectively in Example 16.

Results of agarose gel electrophoresis analysis: As shown in FIG. 11, the method in this invention is used for β-actin-mRNA amplification of RNA samples obtained from about 20 mg rape leaves and the comparison between the obtained DNA product pieces and the DNA product fragment obtained from the 50 mg rape leaves RNA samples using Trizol reagent method shows that the brightness of the former is many times that of the latter.

Summary of Example 16: The extraction of the sample of rape leaves RNA using this method has better Enzymology effect than the extraction of the sample of rape leaves RNA using Trizol reagent method.

In this invention, the preferred monovalent cation salt options are sodium chloride and lithium chloride. But the experiments show that at least one of the other monovalent cation salt options like, rubidium chloride, cesium chloride, lithium acetate, sodium acetate, sodium acetate, potassium acetate, rubidium acetate, cesium acetate, guanidine hydrochloride, guanidine thiocyanate, ammonium chloride, ammonium acetate can also be used to extract RNA.

The experiments show that the precipitating agent options can also be one of the following: rubidium chloride, cesium chloride, lithium acetate, sodium acetate, sodium acetate, potassium acetate, rubidium acetate, cesium acetate, guanidine hydrochloride, guanidine thiocyanate, ammonium chloride and ammonium acetate.

Example 17

Extraction of the Tissue of a Variety of Plants and Animals

The method for isolating and purifying RNA from biological materials includes the following steps:
(1) Add 1 mL formamide stored at 4° C. to four 1.5 ml centrifuge tubes respectively and then add 100 mg of fresh and mature poplar leaves and mouse (Beijing White No. 1, were purchased from Institute of Hematology, Chinese Academy of Medical Sciences) heart, mouse lungs, mouse thigh muscle respectively and conduct electric homogenizing at 26500 rpm for 20 s;
(2) Add 50 μl 5M NaCl aqueous solution to four 1.5 ml centrifuge tubes respectively at room temperature; then add 200 μl of the four dehydrated biological samples obtained in step (1) respectively; after vortex oscillation blending, incubate the centrifuge tubes for 10 min at 90° C. and then keep them at room temperature for 2 min;

Steps (3)~(4) are the same as described in Example 6;

Wash the white RNA precipitate using 1 ml aqueous ethanol solution with volume percentage concentration of 70%; after centrifugation at 16000 g for 10 s at room temperature, discard the washing liquid and dry the precipitate. Add 50 μl water for injection (without RNases contamination) to dissolve the precipitate.

Agarose gel electrophoresis: Same as the agarose gel electrophoresis method described in Example 1.

Results of agarose gel electrophoresis analysis: The 28s rRNA (or 26s rRNA) and 18s rRNA bands obtained from RNA samples are neatly edged and the brightness ratio of them is close to 2:1.

Spectrophotometer: Similar to the method used in Example 3.

Spectrophotometer analysis: The analysis of the yield and purity of the RNA sample extracted from each tissue are shown in Table 3.

TABLE 3

| Tissue | Yield (μg/mg) | OD260/OD280 nm |
|---|---|---|
| Mature poplar leaves | 0.453 | 1.914286 |
| Mouse heart | 0.88 | 2.096774 |
| Mouse lung | 1.184 | 1.902174 |
| Mouse thigh muscle | 0.609 | 2.093023 |

Summary of Example 17: The RNA of a variety of plant and animal tissue can be effectively extracted using the method in this invention Example 18

Relationship Between the Proportion of the Mouse Liver Mass and Formamide Volume and the Yield of RNA Samples The method for isolating and purifying RNA from biological materials includes the following steps:
(1) Add 1 ml formamide stored at 4° C. to seven 1.5 ml centrifuge tubes respectively and then add 10 mg, 25 mg, 50 mg, 100 mg, 200 mg, 400 mg and 800 mg of fresh mouse (Beijing White No. 1, purchased from Institute of Hematology, Chinese Academy of Medical Sciences) liver tissue respectively and conduct electric homogenizing at 26500 rpm for 20 s; this is abandoned because the liquid obtained in the process is viscous with the use of 800 mg mouse liver;
(2) Add 50 μl 5M NaCl aqueous solution to six 1.5 ml centrifuge tubes respectively at room temperature; then add 200 μl of the six dehydrated biological samples obtained in step (1) respectively; after vortex oscillation blending, incubate the centrifuge tubes for 10 min at 90° C. and then keep them at room temperature for 2 min;

Steps (3)~(4) are the same as described in Example 6;

Wash the white RNA precipitate using 1 ml aqueous ethanol solution with volume percentage concentration of 70%; after centrifugation at 16000 g for 10 s at room temperature, discard the washing liquid and dry the precipitate. Add 150 μl water for injection (without RNases contamination) to dissolve the precipitate.

Agarose gel electrophoresis: Same as the agarose gel electrophoresis method described in Example 1.

Results of agarose gel electrophoresis analysis: The bands of the RNA obtained from homogenization of 400 mg mouse liver tissue and 1 ml formamide is at a dispersed state; except for this, the 28s rRNA and 18s rRNA bands obtained from RNA samples are neatly edged and the brightness ratio of them is close to 2:1.

Spectrophotometer: Same as the method used in Example 3.

Figure 12:
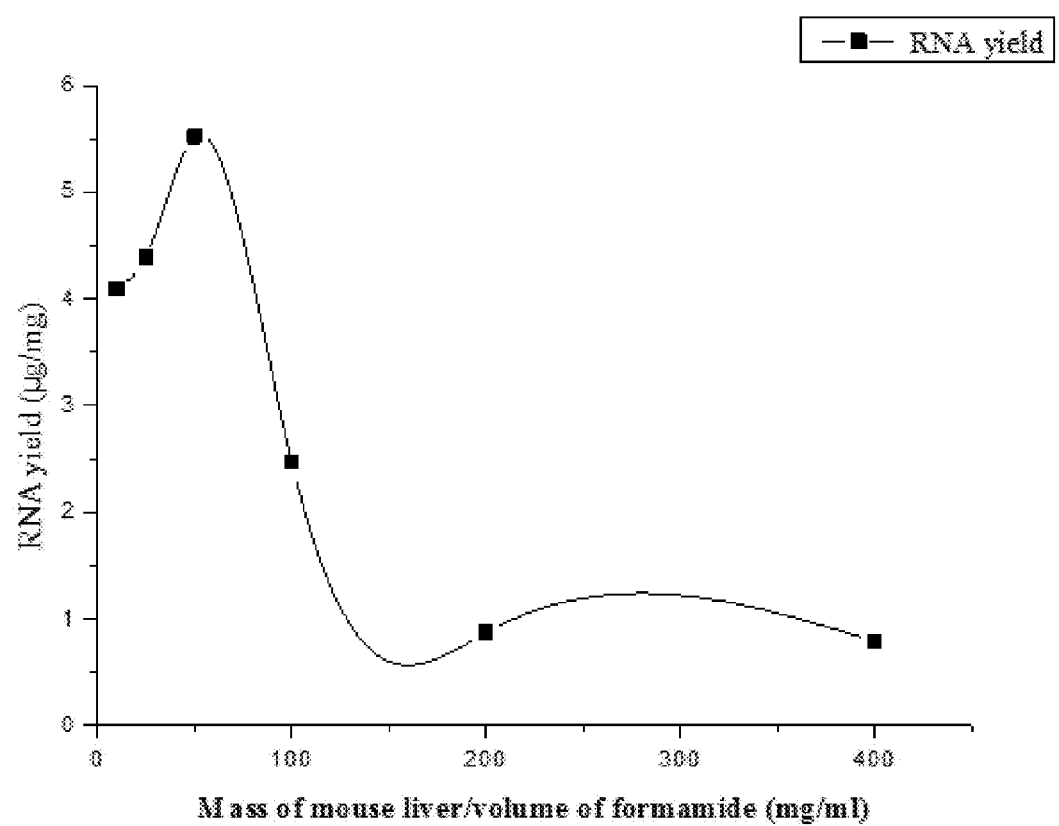
FIG. 12 shows the relationship between the proportion of the mouse liver mass and formamide volume and the yield of RNA samples in Example 18.

Spectrophotometer analysis: The analysis of yield of RNA sample extracted from each tissue is shown in FIG. 12.

Summary of Example 18: In this invention, RNA is extracted through homogenization in the proportion of 1 ml formamide and less than 20 mg of mouse liver tissue and the RNA samples obtained are not decomposed; and the maximum of RNA yield can be obtained through homogenization in the proportion of 1 ml formamide and 5 mg of mouse liver tissue.

Example 19

Correlation Between the Amount of the Volume of the Precipitating Agent, the Amount of the Volume of the Isopropanol, the Salt Particles Precipitated and Liquid Phase in this Invention The method for isolating and purifying RNA from biological materials includes the following steps:
(1) Add 4 ml formamide stored at 4° C. and 0.4 g fresh poplar leaves to one 10 ml centrifuge tube on ice and fully homogenize them; then conduct electric homogenizing three times at 26500 rpm for 20 s;
(2) Prepare fifteen 1.5 ml centrifuge tubes as shown in Table 4 and Table 5; add 50 μl 5M NaCl aqueous solution and 200 μl of the dehydrated biological samples obtained in step (1) to the tubes respectively at room temperature; after vortex oscillation blending, incubate the centrifuge tubes for 10 min at 90° C. and then keep them at room temperature for 2 min;
(3) As shown in Table 4 and Table 5, add 3.57 M NaCl, 1.14 M KCl aqueous solution (precipitant) to 250 μl product obtained in step (2); after vortex oscillation blending and centrifugation at 16000 g for 5 min at room temperature, pour this supernatant into another centrifuge tube;
(4) As shown in Table 4 and Table 5, add isopropanol to the supernatant obtained in step (3); after vortex oscillation blending, leave it at room temperature to observe whether the liquid in the centrifuge tube are divided into two-phased liquid, whether the precipitation of salt particles are generated; and the result is shown in Table 4 and 5; centrifugate at 16000 g for 10 min at 25° C. and discard the liquid and visible residual solid impurities that might suspend in it, the white RNA precipitate can be obtained at the bottom of the centrifuge tube.

Wash the white RNA precipitate using 1 ml aqueous ethanol solution with volume percentage concentration of 70%; after centrifugation at 16000 g for 10 s at room temperature, discard the washing liquid and dry the precipitate. Add 150 μl water for injection (without RNases contamination) to dissolve the precipitate; add 1 ml aqueous ethanol to the centrifuge tube in which salt particles are precipitated and oscillate violently to dissolve the precipitated salt particles.

Agarose gel electrophoresis: Same as the agarose gel electrophoresis method described in Example 1.

Results of agarose gel electrophoresis analysis: As shown in the electrophoresis patterns of the RNA samples, whether the bands of 26s rRNA and 18s rRNA are neatly edged or not determines whether the extracted RNA is decomposed or not. The results are shown in Table 4 and Table 5.

Summary of Example 19: As shown in Table 4 and Table 5, undecomposed RNA product can be obtained when the two-phase liquid appeared after isopropanol is added. That's because all proteins between upper and lower phases are removed, including the enzyme having RNase activity.

TABLE 4

| Number of tubes | 1 | 2 | 3 | 4 | 5 | 6 | 7 |
| --- | --- | --- | --- | --- | --- | --- | --- |
| Precipitant (μl) | 700 | 700 | 700 | 700 | 700 | 700 | 700 |
| Isopropanol (μl) | 200 | 300 | 400 | 500 | 600 | 700 | 800 |
| Precipitate of monovalent cation salt particles | no | no | no | no | yes | yes | yes |
| Generation of upper and lower phase liquid | no | yes | yes | yes | yes | yes | yes |
| Result of RNA electrophoresis | decomposed | undecomposed | undecomposed | undecomposed | undecomposed | undecomposed | undecomposed |

Note:
The precipitating agent is the aqueous solution containing 3.57 MNaCl, 1.14 MKCl.

TABLE 5

| Number of tubes | 8 | 9 | 10 | 11 | 12 | 13 | 14 | 15 |
| --- | --- | --- | --- | --- | --- | --- | --- | --- |
| Precipitant (μl) | 300 | 400 | 500 | 600 | 700 | 800 | 900 | 1000 |
| Isopropanol (μl) | 500 | 500 | 500 | 500 | 500 | 500 | 500 | 500 |
| Precipitate of monovalent cation salt particles | yes | yes | yes | no | no | no | no | no |
| Generation of upper and lower phase liquid | no | yes | yes | yes | yes | yes | yes | yes |
| Result of RNA electrophoresis | decomposed | undecomposed | undecomposed | undecomposed | undecomposed | undecomposed | undecomposed | undecomposed |

Note:
The precipitating agent is the aqueous solution containing 3.57 MNaCl, 1.14 MKCl.

Example 20

The method for isolating and purifying RNA from biological materials includes the following steps:
(1) Same as step (1) described in Example 6;
(2) Add 200 μl mouse liver dehydrated biological sample obtained in step (1) to five 1.5 ml centrifuge tubes respectively at room temperature, then add 50 μl, 100 μl, 150 μl, 200 μl and 250 μl 3M NaCl aqueous solution; after vortex oscillation blending, incubate the centrifuge tubes for 10 min at 90° C. and then keep them at room temperature for 2 min;
Steps (3)-(4) are the same as described in Example 6;
Wash the white RNA precipitate using 1 ml aqueous ethanol solution with volume percentage concentration of 70%; after centrifugation at 16000 g at room temperature for 10 s, discard the washing liquid and dry the precipitate. Add 150 μl water for injection (without RNases contamination) to dissolve the precipitate.

Agarose gel electrophoresis: Same as the agarose gel electrophoresis method described in Example 1.

Results of agarose gel electrophoresis analysis: The 28s rRNA and 18s rRNA bands obtained from RNA samples extracted from the mixture of 50 μl-200 μl 3M NaCl aqueous solution and 200 μl dehydrated biological sample are neatly edged and the brightness ratio of them is close to 2:1.

Summary of Example 20: The RNA of animal tissues can be effectively extracted using the method provided in this invention.

Example 21

The method for isolating and purifying RNA from biological materials includes the following steps:
(1) Add 1 ml formamide solution stored at 4° C. and 100 mg fresh mouse spleen (Beijing White No. 1, purchased from Institute of Hematology, Chinese Academy of Medical Sciences) to the Downce homogenizer on ice and homogenize for 20 s;
(2) Add 160 μl mouse liver dehydrated biological sample obtained in step (1) to four 1.5 ml centrifuge tubes respectively at room temperature, then add 40 μl formamide solution containing sodium dodecyl sulfate with mass volume ratio of 10%, 20%, 30% and 40% and 50 μl 5M NaCl aqueous solution; after vortex oscillation blending, incubate the centrifuge tubes for 10 min at 90° C. and then keep them at room temperature for 2 min;
Steps ((3)-(4) are the same as described in Example 6;
Wash the white RNA precipitate using 1 ml aqueous ethanol solution with volume percentage concentration of 70%; after centrifugation at 16000 g at room temperature for 10 s, discard the washing liquid and dry the precipitate. Add 150 μl water for injection (without RNases contamination) to dissolve the precipitate.

Agarose gel electrophoresis: Same as the agarose gel electrophoresis method described in Example 1.

Results of agarose gel electrophoresis analysis: The 28s rRNA and 18s rRNA bands obtained from the four kinds of RNA samples extracted from the mixture are neatly edged and the brightness ratio of them is close to 2:1.

Summary of Example 21: The RNA of animal tissues can be effectively extracted using the method provided in this invention.

Experiments show that high-quality RNA can also be obtained using 3M NaCl aqueous solution, 10M LiCl aqueous solution or 13.5M LiCl aqueous solution instead of the 5M NaCl aqueous solution used in this example.

Example 22

The method for isolating and purifying RNA from biological materials includes the following steps:
(1) Wash the fresh mouse spleen (Beijing White No. 1, purchased from Institute of Hematology, Chinese Academy of Medical Sciences) with saline in a 10 ml centrifuge tube, and then put the cell suspension liquid in 5 1.5 ml centrifuge tubes, centrifuge at 5000 g at room temperature for 10 min, absorb the liquid, centrifuge again, then remove the residual liquid in the centrifuge tube to obtain single cell precipitate; add 160 μl formamide for suspension at room temperature;
(2) Add 40 μl formamide solution containing sodium dodecyl sulfate with mass volume ratio of 5%, 10%, 20%, 30% and 40% in 5 1.5 ml centrifuge tubes at room temperature for suspension, and then add 50 μl 5M NaCl aqueous solution respectively; after vortex oscillation blending, incubate the centrifuge tubes at 90° C. for 10 min and then keep them at room temperature for 2 min;
Steps (3)-(4) are the same as described in Example 6;
Wash the white RNA precipitate using 1 ml aqueous ethanol solution with volume percentage concentration of 70%; after centrifugation at 16000 g at room temperature for 10 s, discard the washing liquid and dry the precipitate. Add 150 μl water for injection (without RNases contamination) to dissolve the precipitate.

Agarose gel electrophoresis: Same as the agarose gel electrophoresis method described in Example 1.

Results of agarose gel electrophoresis analysis: The 28s rRNA and 18s rRNA bands obtained from the five kinds of RNA samples extracted from the mixture are neatly edged and the brightness ratio of them is close to 2:1.

Summary of Example 22: The RNA of animals' single cells can be effectively extracted using the method provided in this invention.

Experiments show that high-quality RNA can also be obtained by using 200 μl formamide instead of the mixture of formamide and Sodium dodecyl sulfate used in step (1) and step (2), with corresponding changes to the concentration of sodium dodecyl sulfate.

Experiments show that high-quality RNA can also be obtained from the tissues and organs of plants, the tissues and organs of fungi, Gram positive bacteria cultured cells, fungi cultured cells, plant cultured cells, blood cells or sperm cells using the method provided in this invention and by destroying cells with electric homogenizer.

The experiment proves that the RNA obtained using the method provided in this invention and its derivative methods shall also be protected under this invention.

Example 23

The method for isolating and purifying RNA from biological materials includes the following steps:
(1) Add 2 ml formamide solution stored at 4° C. and 200 mg fresh poplar leaves to the 5 Downce homogenizers on ice respectively, and homogenize for 20 s, 1 min, 5 min, 10 min and 20 min respectively;
Steps (2)~(4) are the same as described in Example 6;
Wash the white RNA precipitate using 1 ml aqueous ethanol solution with volume percentage concentration of 70%; after centrifugation at 16000 g for 10 s at room temperature, discard the washing liquid and dry the precipitate. Add 150 µl water for injection (without RNases contamination) to dissolve the precipitate.

Spectrophotometer: Same as the method used in Example 3.

Spectrophotometer analysis: The yields of RNA sample extracted through 20 s, 1 min, 5 min, 10 min and 20 min homogenization are 1.2 µg/mg, 2.2 µg/mg, 2.8 µg/mg, 3.1 µg/mg, and 3.2 µg/mg.

Summary: The more complete tissue homogenization is conducted, the higher the yield of RNA.

Example 24

The method for isolating and purifying RNA from biological materials includes the following steps:
(1) Add 2 ml formamide solution stored at 4° C. and 200 mg fresh poplar leaves to a Downce homogenizers on ice, and homogenize for 5 min;
(2) Add 30 µl 13.5M LiCl aqueous solution and 200 µl dehydrated biological sample obtained in step (1) to a 1.5 ml centrifuge tube in ice; after vortex oscillation blending, incubate the centrifuge tube in ice at 0° C. for 12 hours;

Steps (3)~(4) are the same as described in Example 6;

Wash the white RNA precipitate by using 1 ml aqueous ethanol solution with volume percent concentration of 70%; after 16000 g centrifugation at room temperature for 10 s, discard the washing liquid and dry the precipitate. Add 150 µl water for injection (without RNases contamination) to dissolve the precipitate.

Agarose gel electrophoresis: Same as the agarose gel electrophoresis method described in Example 1.

Results of agarose gel electrophoresis analysis: The 26s rRNA and 18s rRNA bands obtained from the RNA samples extracted from the mixture are neatly edged and the brightness ratio of them is close to 2:1.

Summary: High-quality RNA can be obtained through long-time incubation at low temperature.

What is claimed is:

1. A method for isolating and purifying RNA from biological materials comprising the following steps:
   (1) preparing a dehydrated biological sample by either
      adding tissues and organs to a mixture between formamide and 3M-13.5M monovalent cation salt solution at volume ratio greater than 1 and homogenizing the mixture for 5 seconds to 20 minutes to obtain a dehydrated biological sample; wherein the ratio between the tissues and organs and the mixture is between 05 mg:1 ml and 200 mg:1 ml and the tissues and organs are from animals, plants, or fungi; or
      adding a single-cell precipitate to the mixture between formamide and monovalent cation salt solution at a volume ratio greater than 1, suspending the precipitate at 0~25° C. or homogenizing it at 0~37° C. for 20 seconds to 20 minutes to obtain a dehydrated biological sample; wherein the single cell precipitate is obtained from cultured Gram positive bacteria cells, Gram negative bacteria cells, or fungi cells, cultured cells of animal or plant cells, blood cells or sperm cells;
   (2) mixing the dehydrated biological sample with 3M-13.5M monovalent cation salt solution at a volume ratio greater than 1, or mixing the dehydrated biological sample with 3M-13.5M monovalent cation salt solution and Formamide solution containing sodium dodecyl sulfate of a mass concentration of 5%-40% at a volume ratio of 160:50:40, incubating the resulting mixture at 0~95° C. for 0.5~120 min, and leaving it alone at 0~40° C. for 0~10 min;
   (3) adding 3.3M-5M monovalent cation salt solution to the mixture obtained in step (2) at a volume ratio between 200:1000 and 400:1000 mixing the resulting mixture, centrifuging it in a centrifuge tube for 0.15~30 min at 2000~16000 g at 4~25° C., and then pouring the supernatant into another centrifuge tube;
   (4) adding isopropanol to the supernatant at a volume ratio between 900:300 and 900:800, mixing, centrifuging in a centrifuge tube for 1~30 min at 2000~16000 g at 4~37° C., and then discarding the upper phase liquid, the lower phase liquid and the visible residual solid impurity between the upper and lower phases to get a white RNA precipitate at the bottom of the centrifuge tube.

2. The method according to claim 1, further comprising the following step is: washing the white RNA precipitate using an aqueous ethanol solution at a concentration of 70%-80% by volume; centrifuging for 10~60s at 2000~16000 g at 4~37° C., and then discarding the washing liquid and the precipitate.

3. The method according to claim 1, wherein the ratio between the tissues and organs and the mixture of formamide and monovalent cation salt is between 5 mg:1 ml and 100 mg:1 ml.

4. The method according to claim 1, wherein the monovalent cation salt is lithium chloride, sodium chloride or potassium chloride, or a mixture thereof.

5. The method according to claim 1, wherein the monovalent cation salt is sodium chloride or lithium chloride.

6. The method according to claim 1, wherein the monovalent cation salt used for precipitation is one or more selected from the group consisting of lithium chloride, sodium chloride and potassium chloride.

7. The method according to claim 1, wherein the monovalent cation salt used for precipitation is sodium chloride and potassium chloride.

8. The method according to claim 1, wherein step (4) is as follows: adding isopropanol to the supernatant at a volume ratio between 700:400 and 700:600, mixing, centrifuging in a centrifuge tube for 2 min at 8000~12000 g at 20~25° C., and then discarding the upper phase liquid, the lower phase liquid and the visible residual solid impurities between the upper and lower phases to get a white RNA precipitate at the bottom of the centrifuge tube.

* * * * *